US007972783B2

(12) United States Patent
DeNise et al.

(10) Patent No.: US 7,972,783 B2
(45) Date of Patent: Jul. 5, 2011

(54) METHOD AND MARKERS FOR DETERMINING THE GENOTYPE OF HORNED/POLLED CATTLE

(75) Inventors: Sue DeNise, Davis, CA (US); Emily Oberg, Davis, CA (US); Bonita Ferrie, Vacaville, CA (US); David Rosenfeld, Sacramento, CA (US); Philip Chevalier, West Sacramento, CA (US); Richard Kerr, Davis, CA (US); Michelle Hutton, Davis, CA (US)

(73) Assignee: Branhaven LLC, Canton, OH (US)

( * ) Notice: Subject to any disclaimer, the term of this patent is extended or adjusted under 35 U.S.C. 154(b) by 302 days.

(21) Appl. No.: 11/601,433

(22) Filed: Nov. 17, 2006

(65) Prior Publication Data
US 2007/0134701 A1    Jun. 14, 2007

Related U.S. Application Data

(63) Continuation-in-part of application No. 10/997,814, filed on Nov. 23, 2004, now abandoned.

(60) Provisional application No. 60/525,061, filed on Nov. 24, 2003.

(51) Int. Cl.
*C12Q 1/68* (2006.01)
*C12P 19/34* (2006.01)
*C07H 21/02* (2006.01)

(52) U.S. Cl. ............................ 435/6; 435/91.2; 536/23.1

(58) Field of Classification Search ........................ None
See application file for complete search history.

(56) References Cited

U.S. PATENT DOCUMENTS

| | | | |
|---|---|---|---|
| 4,656,127 A | 4/1987 | Mundy | 435/6 |
| 5,002,867 A | 3/1991 | Macevicz | 435/6 |
| 5,110,745 A | 5/1992 | Kricka et al. | 436/87 |
| 5,304,487 A | 4/1994 | Wilding et al. | 435/29 |
| 5,424,184 A | 6/1995 | Santamaria et al. | 435/6 |
| 5,578,443 A | 11/1996 | Santamaria et al. | 435/6 |
| 5,593,830 A | 1/1997 | Santamaria et al. | 435/6 |
| 5,595,870 A | 1/1997 | Knapp et al. | 435/6 |
| 5,629,149 A | 5/1997 | Santamaria et al. | 435/6 |
| 5,679,524 A | 10/1997 | Nikiforov et al. | 435/6 |
| 5,681,484 A | 10/1997 | Zanzucchi et al. | 216/2 |
| 5,888,819 A | 3/1999 | Goelet et al. | 435/5 |
| 5,919,626 A | 7/1999 | Shi et al. | 435/6 |
| 5,952,174 A | 9/1999 | Nikiforov et al. | 435/6 |
| 5,972,604 A | 10/1999 | Santamaria et al. | 435/6 |
| 6,004,744 A | 12/1999 | Goelet et al. | 435/5 |
| 6,136,962 A | 10/2000 | Shi et al. | 536/23.1 |
| 6,235,473 B1 | 5/2001 | Friedman et al. | 435/6 |
| 6,268,490 B1 | 7/2001 | Imanishi et al. | 536/23.1 |
| 6,287,821 B1 | 9/2001 | Shi et al. | 435/91.2 |
| 6,294,336 B1 | 9/2001 | Boyce-Jacino et al. | 435/6 |
| 6,322,968 B1 | 11/2001 | Head et al. | 435/287.2 |
| 6,337,188 B1 | 1/2002 | Head et al. | 435/6 |
| 6,387,626 B1 | 5/2002 | Shi et al. | 435/6 |
| 6,537,748 B1 | 3/2003 | Goelet et al. | 435/6 |
| 6,872,521 B1 | 3/2005 | Boyce-Jacino et al. | 435/6 |
| 6,946,249 B2 | 9/2005 | Head et al. | 435/6 |
| 2005/0153328 A1 | 7/2005 | DeNise et al. | |

FOREIGN PATENT DOCUMENTS

| | | |
|---|---|---|
| WO | WO 89/10414 | 11/1989 |
| WO | WO 91/02087 | 2/1991 |
| WO | WO 92/15712 | 9/1992 |
| WO | WO 2005/052133 A3 | 6/2005 |

OTHER PUBLICATIONS

Alderborn et al., "Determination of Single-Nucleotide Polymorphisms by Real-time Pyrophosphate DNA Sequencing," *Genome Research*, vol. 10: pp. 1249-1258, (2000).
Asai-Coakwell, "International Conference on Animal Genetics," (in Göttingen-Germany), *International Society for Animal Genetics*, Proceedings (2002).
Brenneman et al., "The Polled Locus Maps to BTA1 in a Bos indicus X Bos Taurus Cross," *The Journal of Heredity*, vol. 87, No. 2: pp. 156-161 (1996).
Cai et al., "Flow Cymetry-Based Minisequencing: A New Platform for High-Throughput Single-Nucleotide Polymorphism Scoring," *Genomics*, vol. 66: pp. 135-143 (2000).
Chee et al., "Accessing Genetic Information with High-Density DNA Arrays," *Science*, vol. 274: pp. 610-614 (1996).
Chen et al., "Florescence Polarization in Homogeneous Nucleic Acid Analysis," *Genome Research*, vol. 9: pp. 492-498(1999).
Clark et al., "Haplotype Structure and Population Genetic Inferences from Nucleotide-Sequence Variation in Human Lipoprotein Lipase," *Am. J. Hum. Genet.*, vol. 63: pp. 595-612 (1998).
Clark, "Inference of Haplotypes from PCR-amplified Samples of Diploid Populations," *Mol. Biol Evol.*, vol. 7, No. 2: pp. 111-122 (1990).
Ecker and Crooke, "Combinatorial Drug Discovery: Which Methods Will Produce the Greatest Value?" *Biotechnology*, vol. 13: pp. 351-360 (1995).
Excoffier and Slatkin, "Maximum-Likelihood Estimation of Molecular Haplotype Frequencies in a Diploid Population," *Mol. Biol. Evol.*, vol. 12, No. 5: pp. 921-927, (1995).
Fan et al., "Parallel Genotyping of Human SNPs Using Generic High-density Oligonucleotide Tag Arrays," *Genome Research*, vol. 10: pp. 853-860, (2000).
Geman and Geman, "Stochastic relaxation, Gibbs distributions, and the Bayesian restoration of images," *IEEE Transactions on Pattern Analysis and Machine Intelligence*, vol. 6: pp. 721-741 (1984).
Georges et al., "Microsatellite Mapping of a Gene Affecting Horn Development in Bos taurus," *Nature Genetics*, vol. 4: pp. 206-210 (1993).
Goonewardene, et al., "A Study of Growth and Carcass Traits in Dehorned and Polled Composite Bulls," *Canadian Journal of Animal Science*, vol. 79: pp. 383-385 (1999).

(Continued)

*Primary Examiner* — Stephen Kapushoc
(74) *Attorney, Agent, or Firm* — Johnson & Associates

(57) ABSTRACT

Provided herein are methods to discover and use single nucleotide polymorphisms (SNP) for determining the genotype of a horned/polled ruminant subject. The present invention further provides specific nucleic acid sequences, SNPs, and SNP patterns that can be used for determining the genotype of a horned/polled ruminant subject.

13 Claims, No Drawings

OTHER PUBLICATIONS

Grossman et al., "High-Density Multiplex Detection of Nucleic Acid Sequences: Oligonucleotide Ligation Assay and Sequence-Coded Separation," *Nucleic Acids Research*, vol. 22, No. 21: pp. 4527-4534 (1994).

Hardenbol et al., "Multiplexed Genotyping with Sequence-tagged Molecular Inversion Probes," *Nature Biotechnology*, vol. 21, No. 6: pp. 673-678 (2003).

Harlizius et al., "New Markers on Bovine Chromosome 1 are Closely Linked to the Polled Gene in Simmental and Pinzgauer Cattle,"*Mammalian Genome*, vol. 8: pp. 255-257 (1997).

Hatch et al., "Rolling Circle Amplification of DNA Immobilized on Solid Surfaces and its Application to Multiplex Mutation Detection," *Genetic Analysis*, vol. 15: pp. 35-40 (1999).

Hermann et al., "Rapid β-Globin Genotyping by Multiplexing Probe Melting Temperature and Color," *Clinical Chemistry*, vol. 46, No. 3: pp. 425-428 (2000).

Jellinek et al., "Potent 2'-Amino-2'Deoxypyrimidine RNA Inhibitors of Basic Fibroblast Growth Factor," *Biochemistry*, vol. 34: pp. 11363-11372 (1995).

Kennedy et al., "Large-scale Genotyping of Complex DNA," *Nature Biotechnology*, vol. 21, No. 10: pp. 1233-1237 (2003).

Kornher and Livak, "Mutation Detection Using Nucleotide Analogs that Alter Electrophoretic Mobility," *Nucleic Acids Research*, vol. 17, No. 19: pp. 7779-7784 (1989).

Kuppuswamy et al., "Single Nucleotide Primer Extension to Detect Genetic Diseases: Experimental Application to Hemophilia B (Factor IX) and Cystic Fibrosis Genes," *Biochemistry*, vol. 88: pp. 1143-1147 (1991).

Labate, "Software for Population Genetic Analyses of Molecular Marker Data," *Crop Science*, vol. 40: pp. 1521-1528 (2000).

Lin et al., "Modified RNA Sequence Pools for in Vitro Selection," *Nucleic Acids Research*, vol. 22, No. 24: pp. 5229-5234 (1994).

Lohmann et al., "Fast and Flexible Single Nucleotide Polymorphism (SNP) Detection with the LightCycler System," *Biochemica*, vol. 4: pp. 23-28 (2000).

Makridakis and Reichardt, Research Report: "Multiplex Automated Primer Extension Analysis: Simultaneous Genotyping of Several Polymorphisms," *BioTechniques* vol. 31, No. 6: pp. 1374-1380 (2001).

Marras et al., "Multiplex Detection of Singe-Nucleotide Variations Using Molecular Beacons," *Genetic Analysis*, vol. 14: pp. 151-156 (1999).

Maxam and Gilbert, "A New Method for Sequencing DNA: DNA Chemistry/Dimethyl Sulfate Cleavage/Hydrazine/Piperidine" *Biochemistry*, vol. 74, No. 2: pp. 560-564 (1977).

Montgomery et al., "Mapping the Horns (Ho) Locus in Sheep: A Further Locus Controlling Horn Development in Domestic Animals," *Journal of Heredity*, vol. 87: pp. 358-363 (1996).

Nairz et al., "High-resolution SNP Mapping by Denaturing HPLC," *PNAS*, vol. 99, No. 16: pp. 10575-10580 (2002).

Nilsson et al., "Padlock Probes: Circularizing Oligonucleotides for Localized DNA Detection," *Science*, vol. 265: pp. 2085-2088 (1994).

Nyren et al., "Solid Phase DNA Minisequencing by an Enzymatic Luminometric Inorganic Pyrophosphate Detection Assay", *Analytical Biochemistry*, vol. 208, pp. 171-175 (1993).

Oliphant et al., "BeadArray™ Technology: Enabling an Accurate, Cost-Effective Approach to High-Throughput Genotyping," *BioTechniques*, vol. 32: pp. S56-S61 (2002).

Pagratis et al., "Potent 2'-amino- and 2'-fluoro-2'-Deoxyribonucleotide RNA Inhibitors of Keratinocyte Growth Factor," *Nature Biotechnology*, vol. 15: pp. 68-73 (1997).

Prezant et al., "Trapped-Oligonucleotide Nucleotide Incorporation (TONI) Assay, a Simple Method for Screening Point Mutations", Human Mutation, vol. 1, pp. 159-164 (1992).

Prince et al., "Robust and Accurate Single Nucleotide Polymorphism Genotyping by Dynamic Allele-Specific Hybridization (DASH): Design Criteria and Assay Validation," *Genome Research*, vol. 11: pp. 152-162 (2001).

Prober et al., "A System for Rapid DNA Sequencing with Fluorescent Chain-Terminating Dideoxynucleotides," *Science*, vol. 238: pp. 336-341 (1987).

Qi et al., "L-RCA (ligation-rolling circle amplification): a General Method for Genotyping of Single Nucleotide Polymorphisms (SNPs)," *Nucleic Acids Research*, vol. 29, No. 22: e116 (7 pages) (2001).

Rao et al., "Genotyping Single Nucleotide Polymorphisms Directly from Genomic DNA by Invasive Cleavage Reaction on Microspheres," *Nucleic Acids Research*, vol. 31, No. 11: e66 (8 pages) (2003).

Ray et al., "Peptide Nucleic Acid (PNA): Its Medical and Biotechnical Applications And Promise for the Future", *The FAESB Journal*, vol. 14: pp. 1041-1060 (2000).

Rhodes et al., "Analysis of the Factor V Leiden Mutation Using the READIT Assay," *Molecular Diagnosis*, vol. 6, No. 1: pp. 55-57 (2001).

Sanger et al., "A Rapid Method for Determining Sequences in DNA by Primed Synthesis with DNA Polymerase", *J. Mol. Biol.*, vol. 94, pp. 441-448 (1975).

Sauer et al., "MALDI Mass Spectrometry Analysis of Single Nucleotide Polymorphisms by Photocleavage and Charge-Tagging," *Nucleic Acids Research*, vol. 31, No. 11: e63 (10 pages) (2003).

Schmutz et al., "DNA Marker-Assisted Selection of the Polled Condition in Charolais Cattle", *Mammalian Genome*, vol. 6: pp. 710-713 (1995).

Sokolov, "Primer Extension Technique for the Detection of Single Nucleotide in Genomic DNA," *Nucleic Acids Research*, vol. 18, No. 12: pp. 3671 (1989).

Stephens et al., "A New Statistical Method for Haplotype Reconstruction from Population Data," *Am. J. Hum. Genet.*, vol. 68: pp. 978-989 (2001).

Storm et al., "MALDA-TOF Mass Spectrometry-Based SNP Genotyping", *Methods in Molecular Biology, Single Nucleotide Polymorphisms: Methods and Protocols*, vol. 212: pp. 241-262, (2003).

Syvänen et al., "A Primer-Guided Nucleotide Incorporation Assay in the Genotyping of Apolipoprotein E", *Genomics*, vol. 8: pp. 684-692 (1990).

Syvänen et al., "Identification of Individuals by Analysis of Biallelic DNA Markers, Using PCR and Solid-Phase Minisequencing." *Am. J. Hum. Genet.*, vol. 52: pp. 46-59 (1993).

Tam et al., "Biological Availability and Nuclease Resistance Extend the In Vitro Activity of a Phosphorothioate-3'hydroxypropylamine Oligonucleotide," *Nucleic Acids Research*, vol. 22, No. 6: pp. 977-986 (1994).

Thelwell et al., "Mode of Action and Application of Scorpion Primers to Mutation Detection," *Nucleic Acids Research*, vol. 28, No. 19: pp. 3752-3761 (2000).

Ugozzoli et al., "Detection of Specific Alleles by Using Allele-Specific Primer Extension Followed by Capture on Solid Support", *GATA*, vol. 9, No. 4: pp. 107-112 (1992).

Wilkinson, "Invasive Action—Third Wave Technologies' Invader™ Assays for Nucleic Acid Detection", *The Scientist*, vol. 13, No. 22: p. 16 (1999).

Xu et al., "Multiplexed SNP Genotyping Using the Qbead™ System: a Quantum Dot-encoded Microsphere-based Assay," *Nucleic Acids Research* vol. 31, No. 8: e43 (10 pages) (2003).

Yamane, "MagiProbe: a Novel Fliorescence Quenching-based Oligonucleotide Probe Carrying a Fluorophore and an Intercalator," *Nucleic Acids Research*, vol. 30, No. 19: e97 (8 pages) (2002).

Yu et al., "Electronic Detection of Single-Base Mismatches in DNA with Ferrocene-Modified Probes," *J. Am. Chem. Soc.* vol. 123: pp. 11155-11161 (2001).

METHOD AND MARKERS FOR DETERMINING THE GENOTYPE OF HORNED/POLLED CATTLE

CROSS REFERENCE TO RELATED APPLICATIONS

This application is a continuation-in-part of U.S. application Ser. No. 10/997,814, filed Nov. 23, 2004, which in turn claims the benefit of priority under 35 U.S.C. §19(e) of U.S. Ser. No. 60/525,061, filed Nov. 24, 2003, the entire content of which are incorporated herein by reference.

FIELD OF THE INVENTION

The invention relates to determination of the genotype for the horned/polled phenotype and more specifically to the use of at least one of eleven single nucleotide polymorphisms to determine the phenotype.

BACKGROUND INFORMATION

In the beef and dairy industries, horns on cattle are the cause of several economic and management problems. Horns pose hazards to animal handlers and also to other cattle causing large economic losses due to bruising. Difficulty in calving (dystocia) has been associated with horns and the widespread practice of dehorning young cattle has been shown to be stressful and reduce growth rates (Goonewardene et al., (1999) Can. J. Anim. Sci. 79:383-385).

Polled (hornless) cattle are found in modern breeds and evidence of polled cattle dates back to the Miocene epoch, well before the domestication of cattle. In some breeds (e.g. Angus) the polled condition has been selected for but in others such as Hereford, the breed was established with the horned phenotype. There is increasing pressure from the live export and feedlot trades on producers to sell hornless cattle. Selective breeding with polled cattle is the means of introgressing the polled trait into horned cattle breeds.

A single gene in cattle controls the horn development trait and the polled phenotype is dominant to the horned phenotype. Thus, hornless cattle may be either heterozygous (horned carriers) or homozygous for the polled allele and the ability to distinguish between carriers and non-carriers is crucial to breeding programs. The physical detection of horned or polled cattle is further complicated by the presence of scurs. Scurs are rudimentary horns that are usually small and loosely attached to the head but can be large and attached well enough to make them difficult to distinguish from horns (Brenneman et al. (1996) J Hered 87:156-161), particularly by the untrained. The scur locus maps to bovine chromosome 19 and is thought to be expressed only in conjunction with the heterozygous horned/polled genotype and masked by the homozygous polled condition (Asai-Coakwell (2002) International Society for Animal Genetics; Schmutz et al., (1995) Mamm Genome 6:710-713). Horn growth makes it impossible for scurs to develop at the same spot, but the horned animals can still carry the gene for scurs. Scurs typically do not appear until about 4 months of age and, if left on, stop growing at a few inches. It can sometimes be difficult to distinguish horns from scurs in a young animal. However, the condition (scurs vs horns) can be easily recognized in a mature animal by one skilled in the art. Nevertheless, a definitive genetic test would greatly facilitate the breeding of polled cattle by obviating the need to distinguish scurs from horns at any stage of animal development.

The polled locus has been mapped to the centromeric region of bovine chromosome 1 (BTA1) (Georges et al. (1993) Nature Genet 4:206-210) but the gene has not been identified. The discovery of genetic markers very closely linked to the polled gene would allow the use of marker-assisted selection (MAS) as a breeding tool. Several groups have conducted linkage studies using families segregating for the horned and polled phenotypes with DNA markers (mostly microsatellites). The gene is located near the centromere of BTA1 (Harlizius et al. (1997) Mamm Genome 8:255-257). Linkage was found for several markers but the data were insufficient to order the genes within the markers.

There is currently no commercial genetic test available in the U.S. to distinguish horned and polled alleles. A test is available at Bova-Can laboratories in Canada that uses 4 microsatellite markers but this test requires samples from complete informative families. Along with the sample from the polled animal being tested, they request samples from a horned full-sib and both polled parents. It is recommended that an extended pedigree is provided before it can be determined if the test will be possible.

DNA analysis provides a powerful tool for distinguish horned and polled alleles of individual animals. Single nucleotide polymorphisms (SNP) are likely to become the standard marker for such identification because of the ease of scoring, low cost assay development and high-throughput capability. Compared with other types of DNA markers, single nucleotide polymorphisms (SNPs) are attractive because they are abundant, genetically stable, and amenable to high-throughput automated analysis. In cattle, the challenge has been to identify a minimal set of SNPs with sufficient power for use in a variety of popular breeds and crossbred populations. SNPs are DNA sequence variations that occur when a single nucleotide in the animal mt-DNA or nuclear genome sequence is altered and detected by traditionally direct DNA sequencing protocol. For example, a SNP might change the DNA sequence AAGGCTAA to ATGGCTAA. SNPs occur at one SNP every 1.9 kilobases in the human genome. SNPs can occur in both coding (gene) and noncoding regions of the genome. Many SNPs have no effect on cell function, but it is believed that others could predispose organism to disease or influence their response to a challenge. SNPs are evolutionarily stable—not changing much from generation to generation—making them easier to follow in population studies. SNPs also have properties that make them particularly attractive for genetic studies. They are more frequent than microsatellite markers, providing markers near to or in the locus of interest, some located within the gene (cSNP), which can directly influence protein structure or expression levels, giving insights into functional mechanisms.

Accordingly, there remains a need for methods and compositions that provide information regarding SNP markers that can distinguish between the bovine horned and polled alleles and thus heterozygous and homozygous polled animals.

SUMMARY OF THE INVENTION

The present invention is based, in part, on the discovery of bovine single nucleotide polymorphism (SNP) markers that are associated with, and predictive of, bovine horned and polled genotypes. The term "marker" refers to a sequence in the genome that is known to vary among individuals in a population. Accordingly, the present invention provides methods to discover and use single nucleotide polymorphisms (SNP) for identifying the horned and/or polled genotype of a bovine subject. The present invention further provides specific nucleic acid sequences, SNPs, and SNP patterns that can be used for identifying a horned or polled genotype for a bovine test subject.

A set of markers that can be used individually, or in combination to distinguish homozygous polled individuals from heterozygous polled animals is provided. The markers can also be used to determine the genotype of all horned and polled animals.

In one embodiment, a method for identifying the horned/polled genotype of a bovine subject from a nucleic acid sample of the subject, is provided. The method includes identifying, in the nucleic acid sample, at least one nucleotide occurrence of a single nucleotide polymorphism (SNP) corresponding to the nucleotide at position 300 of any one of SEQ ID NOs:49-64, or complement thereof, wherein the nucleotide occurrence is predictive of the genotype. Generally, the nucleotide occurrence of at least 2 SNPs can be determined. The 2 SNPs can comprise a haplotype, thereby identifying a haplotype allele that is associated with the genotype. The target nucleic acid molecule can be any nucleic acid molecule, including genomic DNA or RNA, either double- or single-stranded.

In another embodiment, a method of generating a genomic pattern of single nucleotide polymorphisms (SNPs), is provided. The method includes obtaining a nucleic acid sample from a bovine test subject; identifying in the nucleic acid sample a plurality of SNPs corresponding to a nucleotide at position 300 of any combination of SEQ ID NOs:49-64, or the complement thereof; and generating the genomic pattern based upon the identified markers. The genomic pattern generally includes about 3, 5, 8, 10, 12, 14, 16, or more, markers. Exemplary patterns include those provided in patterns 1-25 of Table 2. The plurality of SNPs can be selected from the SNPs designated MMBT25314, MMBT25316, MMBT25309, MMBT10497, MMBT25298, MMBT25303, MMBT10498, MMBT25287, MMBT25288, MMBT25289, MMBT25290, MMBT10493, MMBT25281, MMBT25292, MMBT25313 and MMBT25986.

In another embodiment, a panel of SNPs including MMBT25314, MMBT25316, MMBT25309, MMBT10497, MMBT25298, MMBT25303, MMBT10498, MMBT25287, MMBT25288, MMBT25289, MMBT25290, MMBT10493, MMBT25281, MMBT25292, MMBT25313 and MMBT25986, is provided.

In yet another embodiment, a genomic pattern as set forth in any one of patterns 1-25 of Table 2, is provided.

In one embodiment, a database including any one of patterns 1-25 of Table 2, is provided. The database can include a plurality of patterns selected from the group consisting of patterns 1-25 of Table 2. "Plurality," as used herein, means two or more of the patterns are included in the database.

In another embodiment, a computer-based method for identifying the horned/polled genotype of a bovine subject is provided. The method includes obtaining a nucleic acid sample from the subject; identifying in the nucleic acid sample a plurality of single nucleotide polymorphisms (SNP) corresponding to the nucleotide at position 300 of any combination of SEQ ID NOs:49-64, or complement thereof; searching a database comprising a plurality of genomic patterns selected from the group consisting of patterns 1-25 of Table 2; retrieving the information from the database; optionally storing the information in a memory location associated with a user such that the information may be subsequently accessed and viewed by the user; and identifying the identifying the horned/polled genotype of a bovine subject.

In other embodiments, kits for determining nucleotide occurrences of SNPs associated with horned or polled genotype in a bovine subject are provided. Such kits can include an oligonucleotide probe, primer, or primer pair, or combinations thereof, for identifying the nucleotide occurrence of at least one single nucleotide polymorphism (SNP) corresponding to position 300 of any one SEQ ID NOs:49-64, or complement thereof. The kits can further include one or more detectable labels.

In another embodiment, a database comprising a plurality of single nucleotide polymorphisms (SNP) selected from at least two of the SNP markers at position 300 of any of SEQ ID NOs:49-64, or complement thereof, is provided.

In yet another embodiment, an isolated single nucleotide polymorphism (SNP) corresponding to a nucleotide at position 300 of any one of SEQ ID NOs:49-64, or the complement thereof, is provided.

In another embodiment, an isolated oligonucleotide comprising any one of SEQ ID NOs:49-64, is provided.

In another embodiment, an isolated oligonucleotide selected from the group consisting of SEQ ID NOs:49-64 is provided.

In yet another embodiment, a method for identifying the horned/polled genotype of a ruminant subject from a nucleic acid sample of the subject is provided. The method includes identifying, in the nucleic acid sample, at least one nucleotide occurrence of a single nucleotide polymorphism (SNP) corresponding to the nucleotide at position 300 of any one of SEQ ID NOs:49-64, or complement thereof, wherein the nucleotide occurrence is predictive of the genotype.

In another embodiment, a method of generating a genomic pattern of single nucleotide polymorphisms (SNPs) is provided. The method includes obtaining a nucleic acid sample from a ruminant subject; identifying in the nucleic acid sample a plurality of SNPs corresponding to a nucleotide at position 300 of any combination of SEQ ID NOs:49-64, or the complement thereof; and generating the genomic pattern based upon the identified markers.

In another embodiment, a computer-based method for identifying the horned/polled genotype of a ruminant subject is provided. The method includes obtaining a nucleic acid sample from the subject; identifying in the nucleic acid sample a plurality of single nucleotide polymorphisms (SNP) corresponding to the nucleotide at position 300 of any combination of SEQ ID NOs:49-64, or complement thereof; searching a database comprising a plurality of genomic patterns selected from the group consisting of patterns 1-25 of Table 2; retrieving the information from the database; optionally storing the information in a memory location associated with a user such that the information may be subsequently accessed and viewed by the user; and identifying the identifying the horned/polled genotype of a ruminant subjects. A ruminant subject of the invention includes, but is not limited to, cattle, sheep, buffalo, goats, deer, and giraffes.

The present invention also provides a method for identifying the polled phenotype in a bovine subject, including detecting a dominant polled haplotype allele in a nucleic acid sample from the subject which is selected from GCTCAC, GCTCGC, GATGGG, AATGGG, AATGGC, AATCAC, AATCGG and AATCGC, where the sequence of letters of the haplotype allele represent the nucleotide occurrence of a single nucleotide polymorphism corresponding to nucleotide position 300 of SEQ ID NOs: 53 (marker MMBT25287), 59 (marker MMBT25303), 52 (marker MMBT25281), 63(marker MMBT25316), 62(marker MMBT25314), and 61(marker MMBT25313) respectively. In one embodiment of this method, a diploid pair of haplotype alleles is detected.

The bovine subject can be member of a breed raised for beef production or it can be a member of a breed raised for both beef and milk production. In certain embodiments, the bovine subject is designated by breeding lines as an Angus, Charolais, Gelbvieh, Hereford, Limousin, or Simmental animal.

The invention also provides a method for identifying the horned phenotype in a bovine subject, by detecting a pair of recessive horned haplotype alleles in a nucleic acid sample from the subject, where each haplotype allele is independently selected from GCGCGC, GAGCGG, GAGCGC, GATGGC, GATCAC and GATCGC, where the sequence of letters of the haplotype allele represent the nucleotide occurrence of a single nucleotide polymorphism corresponding to nucleotide position 300 of SEQ ID NOs: 53 (marker MMBT25287), 59 (marker MMBT25303), 52 (marker MMBT25281), 63 (marker MMBT25316), 62 (marker MMBT25314), and 61 (marker MMBT25313) respectively.

The bovine subject can be member of a breed raised for beef production or it can be a member of a breed raised for both beef and milk production. In certain embodiments, the bovine subject is designated by breeding lines as an Angus, Charolais, Gelbvieh, Hereford, Limousin, or Simmental animal.

In another embodiment of the invention, the polled phenotype is identified in a bovine subject by detecting a GATCG haplotype allele in a nucleic acid sample from the subject, where the sequence of letters of the haplotype allele represent the nucleotide occurrence of a single nucleotide polymorphism corresponding to nucleotide position 300 of SEQ ID NOs: 53 (marker MMBT25287), 59 (marker MMBT25303), 52 (marker MMBT25281), 63(marker MMBT25316), 62(marker MMBT25314), and 61(marker MMBT25313) respectively; and also detecting the GATCG haplotype in a nucleic acid sample from at least one polled parent of the subject. In certain aspects of this method, the subject is designated by breeding lines as an Limousin, Jersey, or Holstein animal. In one aspect, the subject is a dairy animal.

Nucleic acids suitable for use in the methods can be isolated from a tissue or bodily fluid of the subject. In one embodiment, the nucleic acid sample is DNA, such as genomic DNA.

Also provided by the invention is a method for identifying a haplotype allele associated with a horned phenotype in a bovine subject, including determining a haplotype in at least one allele of at least one horned bovine subject, where the haplotype allele includes the nucleotide occurrence of a nucleotide polymorphism corresponding to nucleotide position 300 of each of SEQ ID NOs: 53, 59, 52, 63, 62, and 61. In one embodiment, the haplotype of both alleles are detected, and they can be the same or can be different horned haplotypes alleles.

In yet another embodiment, a method for identifying a haplotype allele associated with a polled phenotype in a bovine subject is provided, including detecting the nucleotide occurrence of single nucleotide polymorphisms corresponding to nucleotide position 300 of each of SEQ ID NOs: 53, 59, 52, 63, 62, and 61 in both first and second alleles of a first bovine subject that displays the polled phenotype. According to this method, the horned or polled phenotype of a second bovine subject must also be identified. The second subject is homozygous for the first haplotype allele. If the second subject has a polled phenotype, the first haplotype allele is identified as a haplotype allele associated with the polled phenotype. But when the second subject has a horned phenotype, the first haplotype allele is identified as a haplotype allele associated with the horned phenotype. In one aspect of this method, the first and second alleles of the first bovine subject are the same and therefore it is not necessary to identify the phenotype of a second animal.

Each of the embodiments of the invention can encompass various recitations made herein. It is, therefore, anticipated that each of the recitations of the invention involving any one element or combinations of elements can, optionally, be included in each aspect of the invention.

DETAILED DESCRIPTION OF THE INVENTION

The present invention is based in part on the discovery of single nucleotide polymorphisms (SNPs) that can be used to distinguish between the bovine horned and polled alleles and thus heterozygous and homozygous polled animals. Accordingly, provided herein are methods for generating such information from a nucleic acid sample obtained from a bovine subject, by identifying in the sample, a nucleotide occurrence for at least one single nucleotide polymorphism (SNP), wherein the nucleotide occurrence is associated with the horned or polled genotype.

Using the teachings herein, SNPs associated with horned and polled alleles of any individual animal can be identified. Therefore, methods of the present invention for identifying such a genotype can be used for any bovine subject regardless of breed. For example, the methods can be used to identify horned and polled alleles of an individual animal of a particular breed including, but not limited to, Angus, Limousin, Brahman, Simmental, Hereford, Holstein, Gelbvieh or Charolais cattle. In certain embodiments of the invention, horned and polled alleles can be identified in Jersey or Holstein cattle.

The teachings of invention can be used to identify SNPs and haplotypes useful in the identification of horned and polled alleles of both beef and dairy cattle. For example, identification of SNPs and haplotypes according to the invention is useful in identifying horned and polled alleles in Angus cattle which are a hornless beef breed used as a genetic dehorner, as well as Charolais, Hereford and Limousin breeds, which are used primarily for beef. Similarly the present invention is useful for identification of horned and polled SNPs and haplotypes of cattle raised for both meat and milk production, such as Gelbvieh and Simmental breeds, as well as cattle raised primarily for milk production, such Jersey and Holstein breeds.

Since genomic DNA is double-stranded, each SNP can be defined in terms of either the plus strand or the minus strand. Thus, for every SNP, one strand will contain an immediately 5'-proximal invariant sequence and the other strand will contain an immediately 3'-distal invariant sequence. In one embodiment, a SNP of the present invention can be identified, in part, by its position at nucleotide 300 of any one of the amplicon sequences set forth in SEQ ID NOs:49-64 (see Table 3, infra) in a target nucleic acid sequence. In another embodiment, a SNP of the invention can be identified as present in a nucleic acid sequence resulting from the replication of a nucleic acid sequence by any one of forward oligonucleotide primers SEQ ID NOS:1-16 in combination with any one of reverse oligonucleotide primers SEQ ID NOS:17-32 (see e.g., Table 1, infra).

Nucleic acid molecules having a sequence complementary to that of an immediately 3'-distal invariant sequence of a SNP can, if extended in a "template-dependent" manner, form an extension product that would contain the SNP's polymorphic site. A preferred example of such a nucleic acid molecule is a nucleic acid molecule whose sequence is the same as that of a 5'-proximal invariant sequence of the SNP. "Template-dependent" extension refers to the capacity of a polymerase to mediate the extension of a primer such that the extended sequence is complementary to the sequence of a nucleic acid-template. A "primer" is a single-stranded oligonucleotide (or oligonucleotide analog) or a single-stranded polynucleotide (or polynucleotide analog) that is capable of being extended by the covalent addition of a nucleotide (or nucleotide analog) in a "template-dependent" extension reaction. In order to possess such a capability, the primer must have a 3'-hydroxyl (or other chemical group suitable for polymerase mediated extension) terminus, and be hybridized to a second nucleic acid molecule (i.e. the "template"). A primer is generally composed of a unique sequence of 8 bases or longer complementary to a specific region of the target molecule such that the 3' end of the primer is immediately proximal to a target nucleotide of interests. Typically, the complementary region of the primer is from about 12 bases to about 20 bases.

Single nucleotide polymorphisms (SNPs) are positions at which two alternative bases occur at appreciable frequency (>1%) in a given population, and are the most common type of genetic variation. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Single nucleotide polymorphisms may be functional or non-functional. Functional polymorphisms affect gene regulation or protein sequence whereas non-functional polymorphisms do not. Depending on the site of the polymorphism and importance of the change, functional polymorphisms can also cause, or contribute to diseases.

SNPs can occur at different locations of the gene and may affect its function. For instance, polymorphisms in promoter and enhancer regions can affect gene function by modulating transcription, particularly if they are situated at recognition sites for DNA binding proteins. Polymorphisms in the 5' untranslated region of genes can affect the efficiency with which proteins are translated. Polymorphisms in the protein-coding region of genes can alter the amino acid sequence and thereby alter gene function. Polymorphisms in the 3' untranslated region of gene can affect gene function by altering the secondary structure of RNA and efficiency of translation or by affecting motifs in the RNA that bind proteins which regulate RNA degradation: Polymorphisms within introns can affect gene function by affecting RNA splicing.

The term genotyping or genotype refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Each allele may be present at a different frequency in a given population, for example 30% of the chromosomes in a population may carry the A allele and 70% the C allele. The frequency of the A allele would be 30% and the frequency of the C allele would be 70% in that population. Those individuals who have two copies of the C allele are homozygous for the C allele and the genotype is CC, those individuals who have two copies of the A allele are homozygous for the A allele and the genotype is AA, and those individuals who have one copy of each allele are heterozygous and the genotype is AC.

The Example provided herein illustrates the use of genotyping analysis to identify SNPs that can be used to determine whether a bovine subject possesses a genotype associated with horned or polled phenotypes. The SNP alleles associated with horned or polled genotypes (see e.g., Tables 1 and 3) can be determined using extension oligonucleotide primers (SEQ ID NOS:33-48) to identify particular SNPs in a target nucleic acid sequence. In some embodiments, forward oligonucleotide primers (SEQ ID NO:S:1-16) and reverse oligonucleotide primers (SEQ ID NOS:17-32) were used to amplify specific target sequences prior to extension.

The oligonucleotide primer sequences listed in Table 1 can be used as "sets" of oligonucleotides. For example, the set of oligonucleotides useful for identifying marker MMBT25287 can include SEQ ID NO:8, SEQ ID NO:24 and SEQ ID NO:40, or any combination thereof. The MMBT marker comprises the single nucleotide polymorphism (SNP) corresponding to the nucleotide at position 300, or the complement thereof, of SEQ ID NO:56 (amplicon sequence). SEQ ID NO:8 (forward primer) and SEQ ID NO:24 (reverse primer) can be used to amplify the sequence containing the marker prior to detection. Thus, each set of oligonucleotide primers provides the means for detecting at least one genetic marker useful for determining the genotype of a subject animal. Thus, the "marker set" of oligonucleotide primers for marker MMBT25287 comprises SEQ ID NO:8, SEQ ID NO:24 and SEQ ID NO:40. Such a set of oligonucleotides can be designated "marker set MMBT25287." In addition, the oligonucleotides useful for amplifying a target nucleic acid sequence would include a "primer pair" such as SEQ ID NO:8 and SEQ ID NO:24. A "primer pair" includes a forward and reverse oligonucleotide primer while a "marker set" would include a forward, a reverse and an extension oligonucleotide primer.

Table 1 provides primer sequences (See "Forward," and "Reverse,") that were used to amplify a region that includes the SNP, and amplicon sequences that indicate the nucleotide occurrences for the SNP that were identified in parenthesis within the amplicon sequences provided in Table 3.

As used herein, the term "at least one", when used in reference to a gene, SNP, haplotype, or the like, means 1, 2, 3, 4, 5, 6, 7, 8, 9, 10, etc., up to and including all of the haplotype alleles, genes, haplotypes, and/or SNPs of the bovine genome. Reference to "at least a second" gene, SNP, haplotype or the like, means two or more, i.e., 2, 3, 4, 5, 6, 7, 8, 9, 10, etc., bovine genes, SNPs, haplotypes, or the like.

Polymorphisms are allelic variants that occur in a population that can be a single nucleotide difference present at a locus, or can be an insertion or deletion of one, a few or many consecutive nucleotides. As such, a single nucleotide polymorphism (SNP) is characterized by the presence in a population of one or two, three or four nucleotides (i.e., adenosine, cytosine, guanosine or thymidine), typically less than all four nucleotides, at a particular locus in a genome such as the human genome. It will be recognized that, while the methods of the invention are exemplified primarily by the detection of SNPs, the disclosed methods or others known in the art similarly can be used to identify other types of bovine polymorphisms, which typically involve more than one nucleotide.

In another embodiment, the present invention provides an isolated polynucleotide that includes a fragment of contiguous nucleotides of any one of SEQ ID NOS:33-48, wherein the fragment functions as an extension oligonucleotide in determining the identity of a single nucleotide polymorphism (SNP) corresponding to the nucleotide at position 300, or the complement thereof, of any one of SEQ ID NOS:49-64. In addition, the extension oligonucleotide primer can be at least 90% identical to any one of SEQ ID NOS:33-48, or a complement thereof.

The polynucleotide or an oligonucleotide of the invention can further include a detectable label. For example, the detectable label can be associated with the polynucleotide at a position corresponding to the nucleotide at position 300, or the complement thereof, of any one of SEQ ID NOS:49-64. As discussed in more detail herein, the labeled polynucleotide can be generated, for example, during a microsequencing reaction, such as SNP-IT™ reaction. Detectable labeling of a polynucleotide or oligonucleotide is well known in the art. Particular non-limiting examples of detectable labels include chemiluminescent labels, fluorescent labels, radiolabels, enzymes, haptens, or even unique oligonucleotide sequences.

In another embodiment, the present invention provides an isolated vector that includes a polynucleotide or oligonucleotide disclosed herein. The term "vector" refers to a plasmid, virus or other vehicle known in the art that has been manipulated by insertion or incorporation of a nucleic acid sequence. Methods that are well known in the art can be used to construct vectors, including in vitro recombinant DNA techniques, synthetic techniques, and in vivo recombination/genetic techniques (See, for example, the techniques described in Maniatis et al. 1989 Molecular Cloning A Laboratory Manual, Cold Spring Harbor Laboratory, New York, incorporated herein in its entirety by reference).

In another aspect, the present invention provides a primer pair comprising any one of SEQ ID NOS:1-16 as a first (forward) primer and any one of SEQ ID NOS:17-32 as a second (reverse) oligonucleotide primer. A primer pair will prime polynucleotide synthesis of a target nucleic acid region.

As used herein, "about" means within ten percent of a value. For example, "about 100" would mean a value between 90 and 110.

The term "haplotypes" as used herein refers to groupings of two or more SNPs that are physically present on the same chromosome which tend to be inherited together except when recombination occurs. The haplotype provides information regarding an allele of the gene, regulatory regions or other genetic sequences affecting a trait. The linkage disequilibrium and, thus, association of a SNP or a haplotype allele(s) and a bovine genotype for horned or polled characteristics can be strong enough to be detected using simple genetic approaches, or can require more sophisticated statistical approaches to be identified.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage equilibrium". When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern.

Numerous methods for identifying haplotype alleles in nucleic acid samples are known in the art. In general, nucleic acid occurrences for the individual SNPs are determined and then combined to identify haplotype alleles. There are several algorithms for haplotype reconstruction based on pedigree analysis. These are the Maximum Likelihood methods ((Excofier, L., and Slatkin, M., Mol. Biol. Evol. 12: 921-927 (1995)), the parsimony method created by Clark, A. G., Mol. Biol. Evol. 7: 111-122 (1990) and the phase reconstruction method of Stephens, M., et al., Am. J. Hum. Genet. 68:978-989, 2001, which is incorporated herein by reference). These methods can be applied to the data generated, regarding individual nucleotide occurrences in SNP markers of the subject, in order to determine alleles for each haplotype in a subject's genotype. Alternatively, haplotypes can also be determined directly, for each pair of sites, by allele-specific PCR (Clark, A. G. et al., Am. J. Hum. Genet. 63: 595-612 (1998).

As used herein, the term "infer" or "inferring", when used in reference to the horned or polled genotype of a subject, means drawing a conclusion about the genotype using a process of analyzing individually or in combination, nucleotide occurrence(s) of one or more SNP(s), which can be part of one or more haplotypes, in a nucleic acid sample of the subject, and comparing the individual or combination of nucleotide occurrence(s) of the SNP(s) to known relationships of nucleotide occurrence(s) of the SNP(s) in other bovine animals. As disclosed herein, the nucleotide occurrence(s) can be identified directly by examining nucleic acid molecules, or indirectly by examining a polypeptide encoded by a particular gene where the polymorphism is associated with an amino acid change in the encoded polypeptide.

In diploid organisms such as bovines, somatic cells, which are diploid, include two alleles for each single-locus haplotype. As such, in some cases, the two alleles of a haplotype are referred to herein as a genotype or as a diploid pair, and the analysis of somatic cells, typically identifies the alleles for each copy of the haplotype. Methods of the present invention can include identifying a diploid pair of haplotype alleles. These alleles can be identical (homozygous) or can be different (heterozygous). Haplotypes that extend over multiple loci on the same chromosome include up to 2 to the Nth power alleles where N is the number of loci. It is beneficial to express polymorphisms in terms of multi-locus (i.e. multi SNP) haplotypes because haplotypes offer enhanced statistical power for genetic association studies. Multi-locus haplotypes can be precisely determined from diploid pairs when the diploid pairs include 0 or 1 heterozygous pairs, and N or N−1 homozygous pairs. When multi-locus haplotypes cannot be precisely determined, they can sometimes be inferred by statistical methods. Methods of the invention can include identifying multi-locus haplotypes, either precisely determined, or inferred.

A sample useful for practicing a method of the invention can be any biological sample of a subject, typically a bovine subject, that contains nucleic acid molecules, including portions of the gene sequences to be examined, or corresponding encoded polypeptides, depending on the particular method. As such, the sample can be a cell, tissue or organ sample, or can be a sample of a biological material such as blood, milk, semen, saliva, hair, tissue, and the like. A nucleic acid sample useful for practicing a method of the invention can be deoxyribonucleic (DNA) acid or ribonucleic acids (RNA). The nucleic acid sample generally is a deoxyribonucleic acid sample, particularly genomic DNA or an amplification product thereof. However, where heteronuclear ribonucleic acid, which includes unspliced mRNA precursor RNA molecules and non-coding regulatory molecules such as RNA, is available, a cDNA or amplification product thereof can be used.

Where each of the SNPs of the haplotype is present in a coding region of a gene(s), the nucleic acid sample can be DNA or RNA, or products derived therefrom, for example, amplification products. Furthermore, while the methods of the invention generally are exemplified with respect to a nucleic acid sample, it will be recognized that particular haplotype alleles can be in coding regions of a gene and can result in polypeptides containing different amino acids at the positions corresponding to the SNPs due to non-degenerate codon changes. As such, in another aspect, the methods of the invention can be practiced using a sample containing polypeptides of the subject.

In one embodiment, DNA samples are collected and stored in a retrievable barcode system, either automated or manual, that ties to a database. Collection practices include systems for collecting tissue, hair, mouth cells or blood samples from individual animals at the same time that ear tags, electronic identification or other devices are attached or implanted into the animal. All identities of animals can be automatically uploaded into a primary database. Tissue collection devices can be integrated into the tool used for placing the ear tag. Body fluid samples can be collected and stored on a membrane bound system. The sample is then analyzed on the premises or sent to a laboratory where a medium to high-throughput genotyping system is used to analyze the sample. The subject of the present invention can be any bovine subject, for example a bull, a cow, a calf, a steer, or a heifer or any bovine embryo or tissue.

In another aspect, the present invention provides a system for determining the nucleotide occurrences in a population of bovine single nucleotide polymorphisms (SNPs). The system typically includes a hybridization medium and/or substrate that includes at least two oligonucleotides of the present invention, or oligonucleotides used in the methods of the present invention. The hybridization medium and/or substrate are used to determine the nucleotide occurrence of bovine SNPs that are associated with horned or polled genotypes. Accordingly, the oligonucleotides are used to determine the nucleotide occurrence of bovine SNPs that are associated with the horned or polled genotype. The determination can be made by selecting oligonucleotides that bind at or near a genomic location of each SNP of the series of bovine SNPs. The system of the present invention typically includes a reagent handling mechanism that can be used to apply a reagent, typically a liquid, to the solid support. The binding of an oligonucleotide of the series of oligonucleotides to a polynucleotide isolated from a genome can be affected by the nucleotide occurrence of the SNP. The system can include a mechanism effective for moving a solid support and a detection mechanism. The detection method detects binding or tagging of the oligonucleotides.

Accordingly, in another embodiment, the present invention provides a method for determining a nucleotide occurrence of a single nucleotide polymorphism (SNP) in a bovine sample, that includes contacting a bovine polynucleotide in the sample with an oligonucleotide (e.g., any one of SEQ ID NOS:33-48) that binds to a target nucleic acid region and identifies the nucleotide occurrence of a single nucleotide polymorphism (SNP) corresponding to the nucleotide at position 300 of any one of SEQ ID BOS:49-64. The nucleotide can be detected by amplification or it can be detected based on the lack of incorporation of a specific nucleotide.

In another aspect, forward and reverse primers can be used to amplify the bovine polynucleotide target nucleic acid using a pair of oligonucleotides that constitute a primer pair, and the nucleotide occurrence is determined using an amplification product generated using the primer pair. For example, the primer pair, is any of the forward and reverse primer pairs listed in Table 1.

Medium to high-throughput systems for analyzing SNPs, known in the art such as the SNPStream™ UHT Genotyping System (Beckman/Coulter, Fullerton, Calif.) (Boyce-Jacino and Goelet Patents), the Mass Array™ system (Sequenom, San Diego, Calif.) (Storm, N. et al. (2002) Methods in Molecular Biology. 212: 241-262.), the BeadArray™ SNP genotyping system available from Illumina (San Diego, Calif.)(Oliphant, A., et al. (June 2002) (supplement to Biotechniques), and TaqMan™ (Applied Biosystems, Foster City, Calif.) can be used with the present invention. However, the present invention provides a medium to high-throughput system that is designed to detect nucleotide occurrences of bovine SNPs, or a series of bovine SNPs that can make up a series of haplotypes. Therefore, as indicated above the system includes a solid support or other method to which a series of oligonucleotides can be associated that are used to determine a nucleotide occurrence of a SNP for a series of bovine SNPs that are associated with a trait. The system can further include a detection mechanism for detecting binding of the series of oligonucleotides to the series of SNPs. Such detection mechanisms are known in the art.

The system can be a microfluidic device. Numerous microfluidic devices are known that include solid supports with microchannels (See e.g., U.S. Pat. Nos. 5,304,487, 5,110,745, 5,681,484, and 5,593,838). Numerous methods are known in the art for determining the nucleotide occurrence for a particular SNP in a sample. Such methods can utilize one or more oligonucleotide probes or primers, including, for example, an amplification primer pair that selectively hybridizes to a target polynucleotide, which corresponds to one or more bovine SNP positions. Oligonucleotide probes useful in practicing a method of the invention can include, for example, an oligonucleotide that is complementary to and spans a portion of the target polynucleotide, including the position of the SNP, wherein the presence of a specific nucleotide at the position (i.e., the SNP) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the SNP site is complementary to the corresponding nucleotide of the probe. These oligonucleotides and probes are another embodiment of the present invention.

An oligonucleotide ligation assay (Grossman, P. D. et al. (1994) Nucleic Acids Research 22:4527-4534) also can be used to identify a nucleotide occurrence at a polymorphic position, wherein a pair of probes that selectively hybridize upstream and adjacent to and downstream and adjacent to the site of the SNP, and wherein one of the probes includes a terminal nucleotide complementary to a nucleotide occurrence of the SNP. Where the terminal nucleotide of the probe is complementary to the nucleotide occurrence, selective hybridization includes the terminal nucleotide such that, in the presence of a ligase, the upstream and downstream oligonucleotides are ligated. As such, the presence or absence of a ligation product is indicative of the nucleotide occurrence at the SNP site. An example of this type of assay is the SNPlex System (Applied Biosystems, Foster City, Calif.).

An oligonucleotide also can be useful as a primer, for example, for a primer extension reaction, wherein the product (or absence of a product) of the extension reaction is indicative of the nucleotide occurrence. In addition, a primer pair useful for amplifying a portion of the target polynucleotide including the SNP site can be useful, wherein the amplification product is examined to determine the nucleotide occurrence at the SNP site. Particularly useful methods include those that are readily adaptable to a high throughput format, to a multiplex format, or to both. The primer extension or amplification product can be detected directly or indirectly and/or can be sequenced using various methods known in the art. Amplification products which span a SNP locus can be sequenced using traditional sequence methodologies (e.g., the "dideoxy-mediated chain termination method," also known as the "Sanger Method" (Sanger, F., et al., J. Molec. Biol. 94:441 (1975); Prober et al. Science 238:336-340 (1987)) and the "chemical degradation method," "also known as the "Maxam-Gilbert method" (Maxam, A. M., et al., Proc. Natl. Acad. Sci. (U.S.A.) 74:560 (1977)), both references herein incorporated by reference) to determine the nucleotide occurrence at the SNP locus.

Methods of the invention can identify nucleotide occurrences at SNPs using genome-wide sequencing or "microsequencing" methods. Whole-genome sequencing of individuals identifies all SNP genotypes in a single analysis. Microsequencing methods determine the identity of only a single nucleotide at a "predetermined" site. Such methods have particular utility in determining the presence and identity of polymorphisms in a target polynucleotide. Such microsequencing methods, as well as other methods for determining the nucleotide occurrence at a SNP locus are discussed in Boyce-Jacino, et al., U.S. Pat. No. 6,294,336, incorporated herein by reference, and summarized herein.

Microsequencing methods include the Genetic Bit™ Analysis method disclosed by Goelet, P. et al. (WO 92/15712, herein incorporated by reference). Additional, primer-guided, nucleotide incorporation procedures for assaying polymorphic sites in DNA have also been described (Kornher, J. S. et al, Nucleic Acids Res. 17:7779-7784 (1989); Sokolov, B. P., Nucleic Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al, Hum. Mutat. 1:159-164 (1992); Ugozzoli, L. et al., GATA 9:107-112 (1992); Nyren, P. et al., Anal. Biochem. 208:171-175 (1993); and Wallace, WO89/10414). These methods differ from Genetic Bit™ Analysis in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al. Amer. J. Hum. Genet. (1993) 52:46-59 Other formats for microsequencing include Pyrosequencing (Pyrosequencing AB, Uppsala, Sweden, Alderborn et al (2000) Genome Res. 10:1249-1258).

Alternative microsequencing methods have been provided by Mundy, C. R. (U.S. Pat. No. 4,656,127) and Cohen, D. et al (French Patent 2,650,840; PCT Appln. No. WO91/02087), which discuss a solution-based method for determining the identity of the nucleotide of a polymorphic site. As in the Mundy method of U.S. Pat. No. 4,656,127, a primer is employed that is complementary to allelic sequences immediately 3'- to a polymorphic site.

In response to the difficulties encountered in employing gel electrophoresis to analyze sequences, alternative methods for microsequencing have been developed. Macevicz (U.S. Pat. No. 5,002,867), for example, describes a method for determining nucleic acid sequence via hybridization with multiple mixtures of oligonucleotide probes. In accordance with such method, the sequence of a target polynucleotide is determined by permitting the target to sequentially hybridize with sets of probes having an invariant nucleotide at one position, and variant nucleotides at other positions. The Macevicz method determines the nucleotide sequence of the target by hybridizing the target with a set of probes, and then determining the number of sites that at least one member of the set is capable of hybridizing to the target (i.e., the number of "matches"). This procedure is repeated until each member of a set of probes has been tested.

Boyce-Jacino, et al., U.S. Pat. No. 6,294,336 provides a solid phase sequencing method for determining the sequence of nucleic acid molecules (either DNA or RNA) by utilizing a primer that selectively binds a polynucleotide target at a site wherein the SNP is the most 3' nucleotide selectively bound to the target.

The occurrence of a SNP can be determined using denaturing HPLC such as described in Nairz K et al (2002) Proc. Natl. Acad. Sci. (U.S.A.) 99:10575-80, and the Transgenomic WAVE® System (Transgenomic, Inc. Omaha, Nebr.).

Oliphant et al. report a method that utilizes BeadArray™ Technology that can be used in the methods of the present invention to determine the nucleotide occurrence of a SNP (supplement to Biotechniques, June 2002). Additionally, nucleotide occurrences for SNPs can be determined using a DNAMassARRAY system (SEQUENOM, San Diego, Calif.). This system combines proprietary SpectroChips™, microfluidics, nanodispensing, biochemistry, and MALDI-TOF MS (matrix-assisted laser desorption ionization time of flight mass spectrometry).

As another example, the nucleotide occurrences of bovine SNPs in a sample can be determined using the SNP-IT™ method (Beckman Coulter, Fullerton, Calif.). In general, SNP-IT™ is a 3-step primer extension reaction. In the first step a target polynucleotide is isolated from a sample by hybridization to a capture primer, which provides a first level of specificity. In a second step the capture primer is extended from a terminating nucleotide triphosphate at the target SNP site, which provides a second level of specificity. In a third step, the extended nucleotide trisphosphate can be detected using a variety of known formats, including: direct fluorescence, indirect fluorescence, an indirect calorimetric assay, mass spectrometry, fluorescence polarization, etc. Reactions can be processed in 384 well format in an automated format using a SNPstream™ instrument (Beckman Coulter, Fullerton, Calif.). Reactions can also be analyzed by binding to Luminex biospheres (Luminex Corporation, Austin, Tex., Cai. H. (2000) Genomics 66(2):135-43).

Additional formats for SNP detection include TaqMan™ (Applied Biosystems, Foster City, Calif.), Rolling circle (Hatch et al (1999) Genet. Anal. 15: 35-40, Qi et al (2001) Nucleic Acids Research Vol. 29 e116), fluorescence polarization (Chen, X., et al. (1999) Genome Research 9:492-498), SNaPShot (Applied Biosystems, Foster City, Calif.) (Makridakis, N. M. et al. (2001) Biotechniques 31:1374-80.), oligo-ligation assay (Grossman, P. D., et al. (1994) Nucleic Acids Research 22:4527-4534), locked nucleic acids (LNA™, Link, Technologies LTD, Lanarkshire, Scotland, EP patent 1013661, U.S. Pat. No. 6,268,490), Invader Assay (Aclara Biosciences, Wilkinson, D. (1999) The Scientist 13:16), padlock probes (Nilsson et al. Science (1994), 265: 2085), Sequence-tagged molecular inversion probes (similar to padlock probes) from ParAllele Bioscience (South San Francisco, Calif.; Hardenbol, P. et al. (2003) Nature Biotechnology 21:673-678), Molecular Beacons (Marras, S. A. et al. (1999 Genet Anal. 14:151-156), the READIT™ SNP Genotyping System from Promega (Madison, Wis.) (Rhodes R. B. et al. (2001) Mol Diagn. 6:55-61), Dynamic Allele-Specific Hybridization (DASH) (Prince, J. A. et al. (2001) Genome Research 11:152-162), the Qbead™ system (quantum dot encoded microspheres conjugated to allele-specific oligonucleotides) (Xu H. et al. (2003) Nucleic Acids Research 31:43), Scorpion primers (similar to molecular beacons except unimolecular) (Thelwell, N. et al. (2000) Nucleic Acids Research 28:3752-3761), and Magiprobe (a novel fluorescence quenching-based oligonucleotide probe carrying a fluorophore and an intercalator) (Yamane A. (2002) Nucleic Acids Research 30:e97). In addition, Rao, K. V. N. et al. ((2003) Nucleic Acids Research. 31:66), recently reported a microsphere-based genotyping assay that detects SNPs directly from human genomic DNA. The assay involves a structure-specific cleavage reaction, which generates fluorescent signal on the surface of microspheres, followed by flow cytometry of the microspheres. With a slightly different twist on the Sequenom technology (MALDI), Sauer et al. ((2003) Nucleic Acids Research 31:63) generate charge-tagged DNA (post PCR and primer extension), using a photocleavable linker.

The nucleotide occurrence of a SNP can be identified by other methodologies as well as those discussed above. For example, the identification can use microarray technology, which can be performed with PCR, for example using Affymetrix technologies and GenFlex Tag arrays (See e.g., Fan et al (2000) Genome Res. 10:853-860), or using a bovine gene chip containing proprietary SNP oligonucleotides (See e.g., Chee et al (1996), Science 274:610-614; and Kennedy et al. (2003) Nature Biotech 21:1233-1237) or without PCR, or sequencing methods such as mass spectrometry, scanning electron microscopy, or methods in which a polynucleotide flows past a sorting device that can detect the sequence of the polynucleotide. The occurrence of a SNP can be identified using electrochemical detection devices such as the eSensor™ DNA detection system (Motorola, Inc., Yu, C. J. (2001) J. Am Chem. Soc. 123:11155-11161). Other formats include melting curve analysis using fluorescently labeled hybridization probes, or intercalating dyes (Lohmann, S. (2000) Biochemica 4, 23-28, Herrmann, M. (2000) Clinical Chemistry 46:425).

The SNP detection systems of the present invention typically utilize selective hybridization. As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in identifying a nucleotide occurrence of a SNP. It will be recognized that some amount of non-specific hybridization is unavoidable, but is acceptable provide that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989)).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

The term "polynucleotide" is used broadly herein to mean a sequence of deoxyribonucleotides or ribonucleotides that are linked together by a phosphodiester bond. For convenience, the term "oligonucleotide" is used herein to refer to a polynucleotide that is used as a primer or a probe. Generally, an oligonucleotide useful as a probe or primer that selectively hybridizes to a selected nucleotide sequence is at least about 15 nucleotides in length, usually at least about 18 nucleotides, and particularly about 21 nucleotides or more in length.

A polynucleotide can be RNA or can be DNA, which can be a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (e.g., a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2' deoxyribose, or ribonucleotides such as adenine, cytosine, guanine or uracil linked to ribose. However, a polynucleotide or oligonucleotide also can contain nucleotide analogs, including non naturally occurring synthetic nucleotides or modified naturally occurring nucleotides. Such nucleotide analogs are well known in the art and commercially available, as are polynucleotides containing such nucleotide analogs (Lin et al., Nucleic Acids Research (1994) 22:5220-5234 Jellinek et al., Biochemistry (1995) 34:11363-11372; Pagratis et al., Nature Biotechnol. (1997) 15:68-73, each of which is incorporated herein by reference). Primers and probes can also be comprised of peptide nucleic acids (PNA) (Nielsen P E and Egholm M. (1999) Curr. Issues Mol. Biol. 1:89-104).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., Nucl. Acids Res. (1994) 22:977-986, Ecker and Crooke, BioTechnology (1995) 13:351360), each of which is incorporated herein by reference). The incorporation of non naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide or oligonucleotide comprising nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template. Thus, the term polynucleotide as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR).

In various embodiments for identifying nucleotide occurrences of SNPs, it can be useful to detectably label a polynucleotide or oligonucleotide. Detectable labeling of a polynucleotide or oligonucleotide is well known in the art. Particular non-limiting examples of detectable labels include chemiluminescent labels, fluorescent labels, radiolabels, enzymes, haptens, or even unique oligonucleotide sequences.

A method of the identifying a SNP also can be performed using a specific binding pair member. As used herein, the term "specific binding pair member" refers to a molecule that specifically binds or selectively hybridizes to another member of a specific binding pair. Specific binding pair member include, for example, probes, primers, polynucleotides, antibodies, etc. For example, a specific binding pair member includes a primer or a probe that selectively hybridizes to a target polynucleotide that includes a SNP loci or that hybridizes to an amplification product generated using the target polynucleotide as a template.

As used herein, the term "specific interaction," or "specifically binds" or the like means that two molecules form a complex that is relatively stable under physiologic conditions. The term is used herein in reference to various interactions, including, for example, the interaction of an antibody that binds a polynucleotide that includes a SNP site; or the interaction of an antibody that binds a polypeptide that includes an amino acid that is encoded by a codon that includes a SNP site. According to methods of the invention, an antibody can selectively bind to a polypeptide that includes a particular amino acid encoded by a codon that includes a SNP site. Alternatively, an antibody may preferentially bind a particular modified nucleotide that is incorporated into a SNP site for only certain nucleotide occurrences at the SNP site, for example using a primer extension assay.

A specific interaction can be characterized by a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1 \times 10^{-10}$ M or less. A specific interaction generally is stable under physiological conditions, including, for example, conditions that occur in a living individual such as a human or other vertebrate or invertebrate, as well as conditions that occur in a cell culture such as used for maintaining mammalian cells or cells from another vertebrate organism or an invertebrate organism. Methods for determining whether two molecules interact specifically are well known and include, for example, equilibrium dialysis, surface plasmon resonance, and the like.

In other embodiments, the methods of the invention are useful for generating a "genomic pattern" for an individual genome of a subject. The genomic pattern of a genome indicates the presence or absence of polymorphisms, for example, SNPs, within a genome. Such patterns can be used to identify those bovine subjects comprising a horned or polled genotype. Genomic DNA is unique to each individual subject. Accordingly, the more polymorphisms that are analyzed for a given genome of a subject, the higher probability of generating a unique genomic pattern for the individual from which the sample was isolated. The genomic pattern can be used for a variety of purposes including distinguishing between horned or poled genotypes in a test subject.

Exemplary bovine SNP "genomic patterns" for determining whether a bovine subject possesses the horned or polled haplotype are provided herein. Twenty-five (25) exemplary SNP marker patterns are provided in Table 2. Each pattern comprises a designated "haplotype" (i.e., a series of SNPs identified as being associated with the horned or poled genotype). For example, the haplotype associated with Pattern 1 includes the series of SNPs "GATCGCGG" The SNP series was generated from identifying eight of the sixteen SNPs provided in Table 1. The eight SNPs, set forth in Table 2, include MMBT25287 (G/A), MMBT25303 (C/A), MMBT25281 (T/G), MMBT25316 (G/C), MMBT25314 (G/A), MMBT25313 (G/C), MMBT10493 (G/A), and MMBT25986 (T/G). The predicted genotype, either horned or polled, associated with each pattern is included in Table 2. In one example, the patterns generated from the SNPs provided herein can be utilized to verify the genotype of a cloned animal or frozen or split and/or cloned embryo, or characterize tissues that may undergo intra- or inter-transplantation or propagation to other mammals, or verify the identity of banked and/or frozen semen, or verify cultured cell lines.

In one embodiment of the invention, when a biological sample, such as blood or sperm, is obtained from a bovine test subject, nucleic acid can be isolated and screened with a panel of SNPs to generate a genomic pattern. The genomic pattern can be matched with genomic patterns set forth in patterns 1-25 of Table 2. As noted above, patterns 1-25 were generated using the eight SNPs set forth in Table 2 (e.g., MMBT25287 (G/A), MMBT25303 (C/A), MMBT25281 (T/G), MMBT25316 (G/C), MMBT25314 (G/A), MMBT25313 (G/C), MMBT10493 (G/A), and MMBT25986 (T/G)). However, it is understood that a plurality of these SNPs, in any combination, can be used to generate a genomic pattern. In fact, additional patterns can be generated using all sixteen SNPs, or any combination thereof, as provided in Table 1 and Table 3.

The invention also relates to kits, which can be used, for example, to perform a method of the invention. Thus, in one embodiment, the invention provides a kit for identifying nucleotide occurrences or haplotype alleles of bovine SNPs. Such a kit can contain, for example, an oligonucleotide probe, primer, or primer pair, or combinations thereof for identifying the nucleotide occurrence of at least one bovine single nucleotide polymorphism (SNP) associated with the horned or polled genotype, such as a SNP corresponding to the nucleotide at position 300, or the complement thereof, in any one of SEQ ID NOs:49-64, following hybridization and primer extension. Such oligonucleotides being useful, for example, to identify a SNP or haplotype allele as disclosed herein; or can contain one or more polynucleotides corresponding to a portion of a bovine gene containing one or more nucleotide occurrences associated with a bovine trait, such polynucleotide being useful, for example, as a standard (control) that can be examined in parallel with a test sample. In addition, a kit of the invention can contain, for example, reagents for performing a method of the invention, including, for example, one or more detectable labels, which can be used to label a probe or primer or can be incorporated into a product generated using the probe or primer (e.g., an amplification product); one or more polymerases, which can be useful for a method that includes a primer extension or amplification procedure, or other enzyme or enzymes (e.g., a ligase or an endonuclease), which can be useful for performing an oligonucleotide ligation assay or a mismatch cleavage assay; and/or one or more buffers or other reagents that are necessary to or can facilitate performing a method of the invention.

The primers or probes can be included in a kit in a labeled form, for example with a label such as biotin or an antibody. In one embodiment, a kit of the invention provides a plurality of oligonucleotides of the invention, including one or more oligonucleotide probes or one or more primers, including forward and/or reverse primers, or a combination of such probes and primers or primer pairs. Such a kit also can contain probes and/or primers that conveniently allow a method of the invention to be performed in a multiplex format. The kit can also include instructions for using the probes or primers to determine a nucleotide occurrence of at least one bovine SNPs.

In addition to bovine genomic patterns, it is understood that the SNPs provided herein can be used to generate genomic patterns for other ruminant subjects that possess the horned or polled haplotype. "Ruminant," as used herein, includes any of various hoofed, even-toed, horned mammals of the suborder Ruminantia. Additional exemplary ruminants include sheep, buffalo, goats, deer, and giraffes.

Many software programs for molecular population genetics studies have been developed, their advantage lies in their pre-programmed complex mathematical techniques and ability to handle large volumes of data. Popular programs used by those in the field include, but are not limited to: TFPGA, Arlequin, GDA, GENEPOP, GeneStrut, POPGENE (Labate, J. A., Crop Sci. 40: 1521-1528. (2000)) and Structure. The present disclosure incorporates the use of all of the software disclosed above used to classify bovines into populations based on DNA polymorphisms as well as other software known in the art.

Exemplary markers include the sixteen SNP markers described in Table 1. These markers are in linkage disequilibrium with the horned/polled genotype and can be used alone or in combinations to infer the horned and polled genotypes. Table 3 lists the marker names, extension primer, and the location of the SNP within the amplicon sequence.

Two hundred forty-nine (249) individual animals with known horned/polled phenotype were genotyped for these 16 markers. Some markers are in complete linkage with each other, such that 8 of these markers are sufficient for determining the genotype of an individual animal, as indicated in Example 1 and Table 2. Based on this data, 25 unambiguous haplotypes can be assigned: 14 predict the horned allele and 11 predict the polled allele with perfect accuracy. Table 2 lists the haplotypes in the order: MMBT25287, MMBT25303, MMBT25281, MMBT25316, MMBT25314, MMBT25313, MMBT10493, and MMBT25986, and their predicted genotype, either horned or polled. Haplotype sequences for 8 markers (MMBT25287, MMBT25303, MMBT25281, MMBT25316, MMBT25314, MMBT25313, MMBT10493, and MMBT25986) identify genetic sequence for horned/polled alleles. For example, an animal with the haplotype of GATGGCAG/GAGCGCGG will be horned because both haplotypes represent the horned allele and animals with two copies will have the horned phenotype. An animal with the haplotype GATCGCGT/GCTCACGT will be phenotypically polled, but carries one copy of the horned allele. Finally, an animal with the haplotype AATGGCGG/AATGGGGG will also be phenotypically polled, but the animal carries 2 copies of the polled allele allowing it to breed "true". Similarly, for the six-SNP haplotypes listed in table 5, the combination of GCGCGC/GAGCGG (H/H) predicts a horned phenotype, while GATGGG/AATGGC (P/P) and GAGCGG/GCTCAC (H/P) predict polled phenotypes.

Further analysis permitted identification of nine additional haplotypes predictive for the horned or polled genotype, as indicated below in Example 2. Furthermore, for a significant percentage of cattle, an accurate determination can be performed using haplotypes of only 6 of the 8 SNPs (Example 3).

While most of the animals analyzed according to the invention were beef cattle, the present invention is equally applicable to dairy cattle. For example, the experiments detailed in Example 4 included Jersey and Holstein cattle, both dairy breeds. Jersey and Holstein cattle are generally horned. However, recently new "polled" animals have appeared within these breeds. Following methods of the present invention, a six SNP haplotype has been identified that predicts the polled genotype in these animals.

Listing of Tables

TABLE 1

Marker Name, Forward and Reverse Primer and Single-Nucleotide Polymorphism Allele.

| SNP | FORWARD PRIMER | REVERSE PRIMER | SNP Allele 1 | SNP Allele 2 |
| --- | --- | --- | --- | --- |
| MMBT25314 | TTTTATTTCT CTCTCCCACT CATG (SEQ ID NO 14) | ATTTCATGAT GGGCCTCAG (SEQ ID NO 30) | G | A |
| MMBT25316 | AAACAATTTC ATAAGCCATC CT (SEQ ID NO 15) | GGGGCACCAA GGTAGTCA (SEQ ID NO 31) | G | C |
| MMBT25309 | TGTTTGCAAA AGGAAGAAAA TG (SEQ ID NO 12) | TCTCTCTTTT TTAATGTTTC ACTTGC (SEQ ID NO 28) | C | A |
| MMBT10497 | ACACTAAACC AACAGACAAT AATGAG (SEQ ID NO 1) | TTACAAGTGT TCCCTTTATG GAGT (SEQ ID NO 17) | T | C |
| MMBT25298 | ACTTGATCCT TGTCTTTGCC (SEQ ID NO 10) | TGAGTACCAT ATTGATCCTA AAAACTG (SEQ ID NO 26) | T | C |

TABLE 1-continued

Marker Name, Forward and Reverse Primer and Single-Nucleotide Polymorphism Allele.

| SNP | FORWARD PRIMER | REVERSE PRIMER | SNP Allele 1 | SNP Allele 2 |
|---|---|---|---|---|
| MMBT25303 | AAACTTGTCT GTTGTACTCA AGCA (SEQ ID NO 11) | GCTTAGTAGC TCTGAGGCAT CTT (SEQ ID NO 27) | C | A |
| MMBT10498 | TTTTTGTTCC TATTGTTTTC ATGC (SEQ ID NO 65) | AGACTCCAGG AAACAAATGG A (SEQ ID NO 66) | T | C |
| MMBT25287 | TCTGTAAACA CAGCAGAYCTT TCT (SEQ ID NO 5) | AGCCAAAGAA ACTGAAAAAC TTC (SEQ ID NO 21) | G | A |
| MMBT25288 | TTTTCCRACC ATTTTCAGG (SEQ ID NO 6) | TTCACCCCAG GCCAGAGG (SEQ ID NO 22) | G | A |
| MMBT25289 | AACACGTGAA GTTTTTCAGT TTC (SEQ ID NO 7) | AGAAGCTGAA TGGGGCCA (SEQ ID NO 23) | G | A |
| MMBT25290 | TGAACTGACT GCGCTGGC (SEQ ID NO 8) | TAACACATCT TCCCCCCTG (SEQ ID NO 24) | G | A |
| MMBT10493 | ATTATTTAGC CTACCACAGT CCC (SEQ ID NO 2) | TCCAAGGCAT GTCAACATT (SEQ ID NO 18) | G | A |
| MMBT25281 | ATGTTGCAGT GAACAAAACA GA (SEQ ID NO 4) | TTTCARTGGA AAAGGGAATC A (SEQ ID NO 20) | T | G |
| MMBT25292 | TTGACAAATG TAACTGTAAG GTTTC (SEQ ID NO 9) | ACAGACCCAT TTCACAGACT G (SEQ ID NO 25) | G | A |
| MMBT25313 | CCAACACAGT CCAACGCA (SEQ ID NO 13) | TTGATCATCC TACACATAAC CGT (SEQ ID NO 29) | G | C |
| MMBT25986 | TCCATCCTCG GAAGGGCA (SEQ ID NO 16) | TGACTGACAG GGACTCATTT TTTATT (SEQ ID NO 32) | T | G |

TABLE 2

Haplotypes Identified for Horned or Polled Genotypes.

| Genomic Pattern | Horned (H) or Polled (P) | Haplotype | MMBT-25287 | MMBT-25303 | MMBT-25281 | MMBT-25316 | MMBT-25314 | MMBT-25313 | MMBT-10493 | MMBT-25986 |
|---|---|---|---|---|---|---|---|---|---|---|
| 1 | H | GATCACAG | G | A | T | C | A | C | A | G |
| 2 | H | GAGCGCGG | G | A | G | C | C | C | G | G |
| 3 | H | GAGCGGGG | G | A | G | C | A | G | A | G |
| 4 | H | GATGGCAG | G | A | T | G | G | C | A | G |
| 5 | P | AATCACGG | A | A | T | C | A | C | G | G |
| 6 | H | GATCGCAG | G | A | T | C | G | C | A | G |
| 7 | H | GATCGCGT | G | A | T | C | C | C | G | T |
| 8 | H | GATCGCGG | G | A | T | C | G | C | G | G |
| 9 | P | GCTCACGG | G | C | T | C | A | C | G | G |
| 10 | H | GATCAGGG | G | A | T | C | A | G | A | G |
| 11 | H | GATCACGG | G | A | T | C | A | C | G | G |
| 12 | H | GATCGGGG | G | A | T | C | G | G | G | G |
| 13 | H | GATCGGGT | G | A | T | C | G | G | G | T |
| 14 | H | GATCACAG | G | A | T | C | A | C | A | G |
| 15 | P | AATCACAG | A | A | C | T | A | C | A | G |
| 16 | P | GATGGGGG | G | A | T | G | G | G | G | G |
| 17 | P | AATGACGG | A | A | T | G | A | C | G | G |
| 18 | P | AATGGGAG | A | A | T | G | G | G | A | G |

TABLE 2-continued

Haplotypes Identified for Horned or Polled Genotypes.

| Genomic Pattern | Horned (H) or Polled (P) | Haplotype | MMBT-25287 | MMBT-25303 | MMBT-25281 | MMBT-25316 | MMBT-25314 | MMBT-25313 | MMBT-10493 | MMBT-25986 |
|---|---|---|---|---|---|---|---|---|---|---|
| 19 | P | GCTCACGT | G | C | T | C | A | C | G | T |
| 20 | P | GCTCGCAG | G | C | T | C | G | C | A | G |
| 21 | P | AATCGCGT | A | A | T | C | G | C | G | T |
| 22 | P | AATCGCGG | A | A | T | C | G | C | G | G |
| 23 | P | AATGGCGT | A | A | T | G | G | C | G | T |
| 24 | P | AATGGCGG | A | A | T | G | G | C | G | G |
| 25 | P | AATGGGGG | A | A | T | G | G | G | G | G |

TABLE 3

List of Extension Primer, Location of the SNP in the Amplicon Sequence

| SNP | EXTENSION PRIMER | AMPLICON SEQUENCE |
|---|---|---|
| MMBT 25314 | CTTTGATTTG AGGGATCAGC CTGCA (SEQ ID NO 46) | TCTTTGCATG TGTGGTTCTC TCCCGCCCCC ATCTAAATAT TTTTATTAAA AAAAATCATG AAAAAAATGTT AGCCCCACTC TATCACCTCA ATCCTAGTTT TTTTCTATTT TGAAATGGCA ACCAGGGGCA CACCTTTCAG CCAGACAAGC ACTGGTGTCC CTAGCAAACA AGAGCTAAAT TCCAGGATGG GGAGGAAGAA CAAGGAAAGC TAGTCCACAC CTCCCATCGC CCCCATGCCC CCCTTTTATT TCTCTCTCCC ACTCATGTTT TTATTCCACT TTTCTCTCCT GGATTGGACR TGCAGGCTGA TCCCTCAAAT CAAAGTTTTC CAGTTGTCAT CTGAGGCCCA TCATGAAATC AGTTTAGTGA GTCACGATTA GAAATTAAAA AAAAAAAAAA AAAAGAATAG TTCAGAAAAC ATCAAAGCAC ATCATACAAA GTAAAGATAA ACACTGTTTA ATAACGGATT CCTTTTAGTT GTGTGTGGTT ATGTTGGGCC AAAAGGCAAA ATGTTTTTCT TACTCTGGGT TGCGATCAAA CCATTCTGAA ATTCCCTGAA GGAGAAGGCG AGAGCAGTAA ACATCAGGGC AAAGGTGGCC (SEQ ID NO 62) |
| MMBT 25316 | CCTCCCGGGT TTCTGAGAAC CTGGC (SEQ ID NO 47) | AGGACCACTG CCCTTGGTAT CAGTGGAGCT TTTGTGGAAA GTGACCCCCT GGTGCCCCTG TCTGGGCATA TTGGTGGGGG GTGGCGTCCT GTGGTCGGGA CCACTGCCCT CGGGTGACCC CGGGGGCTGG TGGACCCTCA CACCGCCTGT GGGCCTGGGC CCCTCCTGGG GAGGCCCGAT ACATGTGATG GGGGTTTCTG ACTTGGAAAC AATTTCATAA GCCATCCTGG GAGTAGGTAA GGCAAGAGGG GCCCCCAGAA CCTCAGGGCC CGATCCTCCC GGGTTTCTGA GAACCTGGCS GCTGTTTTCT TTCCCCCAAC AGACATGACT ACCTTGGTGC CCCCAGTGGC CCCCAAGCTG CAAATCCAGA AGCCTCTCCC ATCTGACTCC TGAGTCATGC CTGACTTTGC ACCACGTCCA CGGGTCTCCT CTGTCCTGGC TCCCTCGCAG CTTCTGGTTG CTGTTTTCTC TTCATCTTGC TGCTTAAATC CAGTGTTTCA CCAAGTGTGT TAGCATCAGC TCTCTTCTCT TTCTGTTCTT TCTTCCTTGT CATTTTATCT TCTCTGCCAA ATACCAGCTT CCACTCTCTA CAGATAATTC (SEQ ID NO 63) |
| MMBT 25309 | AGTTTGTTTT AGCCTTTTCC CCTCC (SEQ ID NO 44) | TGAAACAGTC TGTTCATTAT ACAGTCGTAG GACGGAAGAT TTAGCGCTCC CATACCCCGG GACCCGGGCA GGTTACCGTT TTTAGACGGA CAGTTGACAA AAGAATGAAT AGCTCTCTCC TGTCAAATCA GGCTTACAAA CAGCTTGGCA TACAAACAGT TACTACTTGT ATGCATGCGG ATTTAGGGTC CCCACCTGCT AATGCCCCAG ATTTGTAAGT ACAAATTGGT TAGTCTTCAA ACTGTTTGCA AAAGGAAGAA AATGACCAAA AATTAGTTTG TTTTAGCCTT TTCCCCTCCM CTCCCCTCCC TGCTCCTGCA AGTGAAACAT TAAAAAAGAG AGAGAGACAG ACAGAAGAAA AGGATAAAAT AGTATGTAAT AGTCTCGTGG AATATTGTTG GCTTTTTTTA CTTAAGGCAT CGAATGAAGC TGGATCATTG TTTGGTAGGA AATATTTTTG TGCTGCTCAG GCATCCTGCT TCTCAGCAAG CAGCTGAAAA TCTAATAGAA TTAATTGAAG ACCTGTGATG TTAAAAGATG GAGGGGAGGA GATNNNNNNN NNNNNNNNNN NNNNNNNNNN NNNNNNNNNN NNNNNNNNNN (SEQ ID NO 60) |
| MMBT 10497 | GGTCCACTTG ATCCTTGTCT TTGCC (SEQ ID NO 33) | TTTTCTTTTT TTTTAATATA TGAAACTAAT CATAACAAGT GGTTGCTGTG AAAACAGCAG GCTCCCTAAG GCTGCCCTTC CAATGACCCA TACCCTGACC TGGACAGACC ACCTTCTTTC CAAGAGAGGA GAAGTTTTGT TCCTAGATCA GATGAAACTC TGGCTTTACC CCTGGTGACC AGGAGGATTA ATCAGACGCC AGTAAAACAG CCGACAGACA CACTAAACCA ACAGACAATA ATGAGCACAC ACACCAGGAA ACGTCCGTCC AAGAGGTCCA CTTGATCCTT GTCTTTGCCY TAAGATGTAA TACCTGCTCC GTGGCTTGGC TCTCYGTACT CCATAAAGGG AACACTTGTA AGCTGAGAAG CTGCCAGTTT TTAGGATCAA TATGGTACTC ACAAGAGCTG GTTAGGAAAC AATGCCAGGG ACAGAATTTG CAGTGGGGC TTGTGAGGGA TTAGGCTGTT TCCTCAAGAT TTACGTCCCA GTGCACAGCC GGTGCTGAAA CCTGCACGGC CCACCCTGTG GCTCCAGATG AGGTGAATGG AGGTCTCTTT GGGTTTTGGT TTTTCAAAG TAAATCTTC CCAGTGTGCA (SEQ ID NO 49) |

TABLE 3-continued

List of Extension Primer, Location of the SNP in the Amplicon Sequence

| SNP | EXTENSION PRIMER | AMPLICON SEQUENCE |
|---|---|---|
| MMBT 25298 | ATACCTGCTC CGTGGCTTGG CTCTC (SEQ ID NO 42) | CAAGTGGTTG CTGTGAAAAC AGCAGGCTCC CTAAGGCTGC CCTTCCAATG ACCCATACCC TGACCTGGAC AGACCACCTT CTTTCCAAGA GAGGAGAAGT TTTGTTCCTA GATCAGATGA AACTCTGGCT TTACCCCTGG TGACCAGGAG GATTAATCAG ACGCCAGTAA AACAGCCGAC AGACACACTA AACCAACAGA CAATAATGAG CACACACACC AGGAAACGTC CGTCCAAGAG GTCCACTTGA TCCTTGTCTT TGCCYTAAGA TGTAATACCT GCTCCGTGGC TTGGCTCTCY GTACTCCATA AAGGGAACAC TTGTAAGCTG AGAAGCTGCC AGTTTTTAGG ATCAATATGG TACTCACAAG AGCTGGTTAG GAAACAATGC CAGGGACAGA ATTTGCAGTG GGGGCTTGTG AGGGATTAGG CTGTTTCCTC AAGATTTACG TCCCAGTGCA CAGCCGGTGC TGAAACCTGC ACGGCCCACC CTGTGGCTCC AGATGAGGTG AATGGAGGTC TCTTTGGGTT TTGGTTTTTT CAAAGTAAAA TCTTCCCAGT GTGCAAACAG GAACCACTAA CACTGAACCA CATGCAGATG (SEQ ID NO 58) |
| MMBT 25303 | GGCTCAGTGG TAAAGAATTT GCCTG (SEQ ID NO 43) | AAGGACTTGC TCCTGATTTT CCTGAGGATC TCTACCATTT AATTAAGAAA GCCGTTGCGG TTTGAAAGCA TCTTGAGAGG AAAAGAAAGG ATAAAGATGC TCAATTGCAT CTGATTCTGA TTGACAGCCC CATTCACTGG TGGGCTGGAT ATTACAAGAC CAAACAAGTC CTTCCCCTCA ACCGGAAATA CACATCTGCA GCATTTGGCT TGATTGCATA AACTTGTCTG TTGTACTCAA GCAATAAAAC TAGAAAGAAA GGGRTTTCCC AGGTGGCTCA GTGGTAAAGA ATTTGCCTGM CAATGCAGGA GATACGGATT CGATYCCTGG GCCAGGAAGA TGCCTCAGAG CTACTAAGCC CAAGCACTAC AATTACTGAG MCCAYGTGCC ACAAGCCTGA ACACCCTAGA GTGTAKGCTC CACCACAAAA GAAGCTCCCA CAGCGAGGAG CCTTCACACC ACAACTGGAC TGTCACCTCR CCTAGCAGCA ACTAGAGAAA AGTCTGCACA GCAATAAAGA CCCAGCACAG CCATAAATAA AATTATTTTT TAAAGGACTA GGAAAAAAAA AGAAAGAAAA TATATCCAAA ATATGACCAC (SEQ ID NO 59) |
| MMBT 10498 | GGCTTCTGTC TGTAAACACA GCAGA (SEQ ID NO 35) | GAAAAAAAAC CCCACCCATT TCATTTGGAC TGTGTACTAA GAATAATTGC CACCAATATT GATTGGCCCT TGGGGACCCA GCTGAATTTA AAAATTGCAG ACTGTGAAAT CCCAGCTGAT ATAGCCTCGT GGAGCTTGCT GCTTATTTGT GACATGTTCC TATGTTTAAA CTTACCCACA AAAACTGTGA AATTAATATC CTCACGTTGA GTACAATATG GTGACACACC CAGCTGACAT GCGCAGCTAT TTTTGTTCCT ATTGTTTTCA TGCTGGCTTC TGTCTGTAAA CACAGCAGAY CTTTCTGATG ATGAAGCATA AGTCCATTTG TTTTCCTGGAG TCTCCTTTTC CRACCATTTT CAGGGGTTGG GCCAACACGT GAAGTTTTTC AGTTTCTTTG GCTGCACRTT TCGCTGTAAT GAGTCAACGC AGCAGGGTCT CCCRGTGGCC TCTGGCCTGG GGTGAACTGA CTGCGCTGGC CCCATTCAGC TTCTCCTTGG CTATGCCTRC CTCTAGCACA GGCAGCTTGA AGCTAGACAT TCCTGTTAAA AGCAGGGGGG AAGATGTGTT AGTTTGCCTA AATCCACGTA ATGAAGGATG (SEQ ID NO 51) |
| MMBT 25287 | TTTGTTTCCT GGAGTCTCCT TTTCC (SEQ ID NO 37) | CCAATATTGA TTGGCCCTTG GGGACCCAGC TGAATTTAAA AATTGCAGAC TGTGAAATCC CAGCTGATAT AGCCTCGTGG AGCTTGCTGC TTATTTGTGA CATGTTCCTA TGTTTAAACT TACCCACAAA AACTGTGAAA TTAATATCCT CACGTTGAGT ACAATATGGT GACACACCCA GCTGACATGC GCAGCTATTT TTGTTCCTAT TGTTTTCATG CTGGCTTCTG TCTGTAAACA CAGCAGAYCT TTCTGATGAT GAAGCATAAG TCCATTTGTT TCCTGGAGTC TCCTTTTCCR ACCATTTTCA GGGGTTGGGC CAACACGTGA AGTTTTTCAG TTTCTTTGGC TGCACRTTTC  GCTGTAATGA GTCAACGCAG CAGGGTCTCC CRGTGGCCTC TGGCCTGGGG TGAACTGACT GCGCTGGCCC CATTCAGCTT CTCCTTGGCT ATGCCTRCCT CTAGCACAGG CAGCTTGAAG CTAGACATTC CTGTTAAAAG CAGGGGGGAA GATGTGTTAG TTTGCCTAAA TCCACGTAAT GAAGGATGAC TACGTAGACT TGCACGTACA TGGATTGCAA GCTTCAAATA TGTCAAGGAT (SEQ ID NO 53) |
| MMBT 25288 | GCTGCGTTGA CTCATTACAG CGAAA (SEQ ID NO 38) | ATCCCAGCTG ATATAGCCTC GTGGAGCTTG CTGCTTATTT GTGACATGTT CCTATGTTTA AACTTACCCA CAAAAACTGT GAAATTAATA TCCTCACGTT GAGTACAATA TGGTGACACA CCCAGCTGAC ATGCGCAGCT ATTTTTGTTC CTATTGTTTT CATGCTGGCT TCTGTCTGTA AACACAGCAG AYCTTTCTGA TGATGAAGCA TAAGTCCATT TGTTTCCTGG AGTCTCCTTT TCCRACCATT TTCAGGGGTT GGGCCAACAC GTGAAGTTTT TCAGTTTCTT TGGCTGCACR TTTCGCTGTA ATGAGTCAAC GCAGCAGGGT CTCCCRGTGG CCTCTGGCCT GGGGTGAACT GACTGCGCTG GCCCCATTCA GCTTCTCCTT GGCTATGCCT RCCTCTAGCA CAGGCAGCTT GAAGCTAGAC ATTCCTGTTA AAGCAGGGG GGAAGATGTG TTAGTTTGCC TAAATCCACG TAATGAAGGA TGACTACGTA GACTTGCACG TACATGGATT GCAAGCTTCA AATATGTCAA GGATGGAAAT TTCAAATGTT TCTGAAATGA GTCACAACTA AAAATGAAAA GTTAATCCTA (SEQ ID NO 54) |
| MMBT 25289 | CAGTTCACCC CAGGCCAGAG GCCAC (SEQ ID | ATTTGTGACA TGTTCCTATG TTTAAACTTA CCCACAAAAA CTGTGAAATT AATATCCTCA CGTTGAGTAC AATATGGTGA CACACCCAGC TGACATGCGC AGCTATTTTT GTTCCTATTG TTTTCATGCT GGCTTCTGTC TGTAAACACA GCAGAYCTTT CTGATGATGA AGCATAAGTC CATTTGTTTC CTGGAGTCTC |

TABLE 3-continued

List of Extension Primer, Location of the SNP in the Amplicon Sequence

| SNP | EXTENSION PRIMER | AMPLICON SEQUENCE |
|---|---|---|
| | NO 39) | CTTTTCCRAC CATTTTCAGG GGTTGGGCCA ACACGTGAAG TTTTTCAGTT TCTTTGGCTG CACRTTTCGC TGTAATGAGT CAACGCAGCA GGGTCTCCCR GTGGCCTCTG GCCTGGGGTG AACTGACTGC GCTGGCCCCA TTCAGCTTCT CCTTGGCTAT GCCTRCCTCT AGCACAGGCA GCTTGAAGCT AGACATTCCT GTTAAAAGCA GGGGGGAAGA TGTGTTAGTT TGCCTAAATC CACGTAATGA AGGATGACTA CGTAGACTTG CACGTACATG GATTGCAAGC TTCAAATATG TCAAGGATGG AAATTTCAAA TGTTTCTGAA ATGAGTCACA ACTAAAAATG AAAAGTTAAT CCTACGTATC CTTCCTTCTT ACGTCATGAA GATGTACACT (SEQ ID NO 55) |
| MMBT 25290 | AGCTTCAAGC TGCCTGTGCT AGAGG (SEQ ID NO 40) | AGTACAATAT GGTGACACAC CCAGCTGACA TGCGCAGCTA TTTTTGTTCC TATTGTTTTC ATGCTGGCTT CTGTCTGTAA ACACAGCAGA YCTTTCTGAT GATGAAGCAT AAGTCCATTT GTTTCCTGGA GTCTCCTTTT CCRACCATTT TCAGGGGTTG GGCCAACACG TGAAGTTTTT CAGTTTCTTT GGCTGCACRT TTCGCTGTAA TGAGTCAACG CAGCAGGGTC TCCCRGTGGC CTCTGGCCTG GGGTGAACTG ACTGCGCTGG CCCCATTCAG CTTCTCCTTG GCTATGCCTR CCTCTAGCAC AGGCAGCTTG AAGCTAGACA TTCCTGTTAA AAGCAGGGGG GAAGATGTGT TAGTTTGCCT AAATCCACGT AATGAAGGAT GACTACGTAG ACTTGCACGT ACATGGATTG CAAGCTTCAA ATATGTCAAG GATGGAAATT TCAAATGTTT CTGAAATGAG TCACAACTAA AAATGAAAAG TTAATCCTAC GTATCCTTCC TTCTTACGTC ATGAAGATGT ACACTTTCAA CCAAGCAAAA CATATAAACA ACTCTGATGG TGAAATTTTC AGGGCGCCAC GGATTGTTAC (SEQ ID NO 56) |
| MMBT 10493 | ACCTCTAGGT AAGCTTTCGT AAAGC (SEQ ID NO 34) | CGGGCATGCG CACAGCTGAG TCACTTCACT GTACAGCAGA AATTGCTTGA AAAGCAATTA TATTCCCCCC CAAACCAATT ATATTCCCCC AAATTTATAT TTTATATTGA AAAAACTCAG TGGATTGGCA AACTTAATTC TATCCTTCTT AATTCTTAAT TCTATTCTTG AGACTCAGGA ATCTGAATTC CTTCTTGCCA CCTAACCTAA CATATTCATG GGTTCCAGGG ATTAAGAGGG GGACATTATT TAGCCTACCA CAGTCCCGGG CATCACCTCT AGGTAAGCTT TCGTAAAGCR GAAATGCCTC TTTCCCCTTT CTCCAAATGT TGACATGCCT TGGAGGGCAG GCAGGCAGTG GGTTGGAGAA ACAGGTATAT TTAGCAAAAC TGATTCAGCT CTGCCCTCAC TGAGATCCAG TGGATGAAAT GTTATTTTGA AGTAGTATCT GTCTTTTCCC AAACAGCACT TCAGGACTTT TGTGGTGACC TCTCTAAACA CTTCATTTTC ATTCATGAGG AAATGGAGAG CCAGGCGGGA AGGACTTCTC CAGGGTTTCC CAGCGGTTCC CCAGCNNNNN NNNNNNNNNN NNNNNNNNNN (SEQ ID NO 50) |
| MMBT 25281 | CTGCACATCT TCATGGAGTT CACAC (SEQ ID NO 36) | GTTAAGTCTT TACCTTATGG ATGAGAAAAC AGAGATTCAG AAAATCTGAA TCTCTTGACA GAGACACTTG ACAGAGTCAC AGAGCTTTCA TTCACTTAAA AGTCAATGAG AGAATGAGAA AAAGTATTTG AATCACCACT TCACTGAATT ATTCAACATA TGTAACTCTT TCTTATTGGA TTCCCTCATT CATTCATTCT ACAAATATTT ACTGAGTGCC TAGTATGTGC CCATCACTGC TGAGGATGTT GCAGTGAACA AAACAGACAA AGAACTGCAC ATCTTCATGG AGTTCACACK CCAAGGATTC AATAAAATTT AAATCCCTGA TTCCCTTTTC CAYTGAAAGG TCGCTATTTT AACAATTCTA AGAAACCACT TGATTAGCAT CAAAGATGTT GAACAAATGC TCTGTTGACA TAATTTGATG AGTGTAGGAA TTACAAATAT GAGTCAACTY CACTGATTAC AAAGACAGAA GAAAGTAGTG TACAATCAAC TTTTTTAGAA AAGAATTAAA CCCCATGAAA AAACAATGTT CCAACATGAC ATCCAGATTC ACCAGCYATG TCTCCTGAAA CAGAGGAGAA GACTGTTAGG (SEQ ID NO 52) |
| MMBT 25292 | TTTGCCACTG CCACATCCCA GCTRA (SEQ ID NO 41) | NNNNNNCTCT TAATTTACA ATTTTCTACC TGTTACCTGG TACCTGGTAC CAGATAAGAG AAAATACATT TTTTTAAACT AAATTTCTTG TCTACATATA AACCTTCCCA CAAAACTTCG CTATGGGTTA AATATGTATC CAGCCTTGTG ATGAGCACTG GGGGATGAAG ACTTAGCAAC CAAGAGGTAA AGGTCCTAAC CACAGGAAAC TAAGATGCTC TTTTAAATTT TAACCATATA AGGCAGAGTT GACAAATGTA ACTGTAAGGT TTCCTTTGCC ACTGCCACAT CCCAGCTRAR TTGCATAACT CAACTTCTCA ATTTCACAGT CTGTGAAATG GGTCTGTGAG TCAAATCTAC TCYAGCATAG GCATGGGGAT GAAATGCCTG GAAAGATCCA ATCTGGGCAC ACAGTCTTCA CCTCCCCTGT GTGATGGGGA ACAAGCACAG TRGGAAATTC ATGGGAAGGA AAGCTTGCCA TGGGCTGAGC TATGTAGGGG GGACCAGAGG AGGGGTTGAG GATTGACTTG AGAGCATGAG GTAGCCCGGG ATAACATAGA TCATTTTGAT CCAAATTGCT GCTGCGAGCC TGTGATAATT GGGTGA (SEQ ID NO 57) |
| MMBT 25313 | GTGGGGGCGG GCCGGTGCCG CCTCC (SEQ ID NO 45) | CATTTACACG GAAAGCTTTT TCTTTTACTT TGGGATGCAG AGTAACTCCC AAATTACAGA GCCACTTGGC GATTAAGGCA GGATGGAGGT GCATTTGATA ACTTAATGCA ACTTTTTACC AGCACTTAAA ACTACAGATAT GAAATCTACA CTTGATCTTT CCTGCTTGGA ATTGGCCAAA TTAGTGGCTG TATCCCCATG TACAACAAAA GCCTCTCAGA AACACTCAGG GAAGCCGACC AACCAAAGGG CCCAACACAG TCCAACGCAW GCATGTGGGG GCGGGCCGGT GCCGCCTCCS CCTCGAGCCC CTCAAACAGC CTTTCGGCTC CAGACGGTTA TGTGTAGGAT GATCAAGGGT AGACGTGATA CGCTCAAGGT AGAAATGAGG ACTTCAGGGC |

TABLE 3-continued

List of Extension Primer, Location of the SNP in the Amplicon Sequence

| SNP | EXTENSION PRIMER | AMPLICON SEQUENCE |
|---|---|---|
| | | ATGCCTTGCG AGCTTTCTCC AGTTAATTGG AAAATTATAT AGTGATTTCA CTGCTCATAA CAATAAAACC TTCTCTTTTA ACTTTAAAGA TGATGATGAC TGGTGAGCAG CACTATAAAC CTCAGAAAGT TGTCTAGAAG GTTAAAATGA CTGGACTGGA TTTAGGGGAA GGGCAGATTT GCTGCACTTT TTAAAAAAAC (SEQ ID NO 61) |
| MMBT 25986 | GGGCGGAGTG GAGAGGCTGT TCCTG (SEQ ID NO 48) | AACACTTCTA CAAAATTAGG TCAGTCATAT ACTTTTATAA TCAGCTTTTG TACTTAATAA ATTAGACTTT TARTCTGTTC CATATATTCT TCTGCATGTT TTAACAATTG TGTCACACAG CAGGTGGGGR CAGCTTGTCC TCACAGGCTC TGTCAGCACC CTCTCAGCCC GCTACCATGA GCCTCCTCAC AGGAGCACGT TCATACGCAC AGCCTGCCTG GGGCTCAGCT GTGCTGGGGT GAAGCTTTGG GTACTCCATC CTCGGAAGGG CACAGGGCGG AGTGGAGAGG CTGTTCCTGK AAACCTGAGA ACACTGGCAA TAAAAAATGA GTCCCTGTCA GTCAAATAAG TATCCTGTCT GGTGGTGCTG TATATGTTTT CATGTGTTTG TGGTCATTTT ACTTTCTCAT TTGATGTGTT TTACTTGGCA GTTCTTATGG TGTGCAAGGG TTTTTGGGTT TTTTTTTTTA GTTGATTTGT AGGAGCCAGT TTATGTTAAG GATCAGAACC TCTGTATAAT CCATACTTTT CCTACTGGGC CATTTGTATC TTGATTCTCT GTTTTTGTTT TTAATTGAAG GATAATTGCT TTACAATATT (SEQ ID NO 64) |

The following examples are intended to illustrate but not limit the invention.

EXAMPLE 1

Identification of SNP Markers and Haplotypes for Inferring Horned and Polled Phenotypes Approximately 150 biallelic SNP markers within a 1.5 cM region surrounding the known location of the horned/polled locus were analyzed for the nucleotide occurrence of the polymorphism in genomic DNA of 249 animals of known breed and known horned (homozygous recessive) or polled (homozygous dominant or heterozygous) genotype and phenotype. Representative primers used for SNP determination by primer extension are listed in Table 1. The initial analysis was performed on 9 breeds: Holstein, Angus, Red Angus, Limousin, Hereford, Simmental, Salers, Charolais and Gelbvieh. The marker haplotypes observed were common across all breeds analyzed.

Using a Chi-square analysis, 16 markers were selected based on a LOD score >3.0. Based on this selection, each marker had a likelihood about 100 times greater of segregating with the genotype than a marker chosen at random.

The Gibbs Sampler (MCMC technology as described in Geman & Geman, "Stochastic relaxation, Gibbs distributions and the Bayesian restoration of images," IEEE Trans. Pattn. Anal. Mach. Intel., 6, 721-741, 1984.), was used to develop haplotypes from the 16 markers. The initial analysis indicated that 8 markers (MMBT25287, MMBT25303, MMBT25281, MMBT25316, MMBT25314, MMBT25313, MMBT10493 and MMBT25986) were sufficient to accurately and unambiguously determine the genotype of the animals tested. Regardless of breed, detection of one polled haplotype or two horned haplotypes of the eight identified markers inferred the underlying genotype of the animal, across all breeds analyzed Twenty-five haplotypes were observed in the initial 249 animals analyzed as summarized in Table 2, above. The 25 haplotypes were perfectly predictive of genotype and did not require further statistical analysis for determining the genotype of a subject animal. The limited number of haplotypes that were observed is consistent with current teaching of the art suggesting that that not all theoretically possible haplotypes for most traits are actually present in any population. The 25 exemplary haplotypes summarized in Table 2 likely represent the most prevalent haplotypes in the population of cattle studied.

EXAMPLE 2

Identification of Thirty-Four Eight-SNP Haplotypes

Based on the initial identification of eight markers useful for determining horned and polled genotypes, a larger sample of 4171 animals was analyzed. Table 3 lists the number of animals of each breed included in this analysis.

TABLE 3

Animals Tested for Eight SNP Haplotypes by Breed

| breed | Number Analyzed |
|---|---|
| Angus | 39 |
| Ayrshire | 1 |
| Beefmaster | 1 |
| Braford | 1 |
| Braunvieh | 3 |
| Charolais | 41 |
| Cross Breed | 11 |
| Gelbvieh | 426 |
| Hereford | 136 |
| Holstein | 78 |
| Jersey | 8 |
| Limousin | 2699 |
| Piedmontese | 8 |
| Red Angus | 27 |
| Salers | 47 |
| Simmental | 584 |
| Unknown | 61 |
| Total | 4171 |

The haplotypes initially identified in a small research sample were confirmed in the larger sample, while only 13 additional haplotypes were identified. This result supports the initial conclusion that the 25 haplotypes shown in Table 2 describe most of the allelic variation observed in cattle.

New haplotypes were detected by identifying a homozygous animal and associating it with phenotype. For example, detecting an animal with a homozygous 1250/1250 haplotype and a polled phenotype was interpreted to mean that haplotype 1250 is polled. Similarly, an animal with 1090/1090 haplotype and a horned phenotype was interpreted to mean that haplotype 1090 is a horned haplotype. Based on this analysis, 34 haplotypes were assigned to a specific genotype (21 polled and 13 horned) across all breeds tested as indicated in Table 4.

TABLE 4

Eight-SNP Haplotypes and Percentage Representation in 4,171 Cattle of Various Breeds

| Designation | Actual Haplotype[1] | % |
|---|---|---|
| Polled Haplotypes | | |
| 1054 | GCTCACGG | 0.20% |
| 1055 | GCTCACGT | 0.06% |
| 1060 | GCTCGCAG | 15.03% |
| 1061 | GCTCGCAT | 4.83% |
| 1062 | GCTCGCGG | 5.55% |
| 1063 | GCTCGCGT | 0.39% |
| 1104 | GATGGGAG | 0.06% |
| 1106 | GATGGGGG | 1.09% |
| 1120 | GATCGGAG | 0.08% |
| 1232 | AATGGGAG | 0.39% |
| 1234 | AATGGGGG | 8.42% |
| 1235 | AATGGGGT | 1.98% |
| 1238 | AATGGCGG | 2.65% |
| 1239 | AATGGCGT | 1.06% |
| 1244 | AATCACAG | 0.98% |
| 1245 | AATCACAT | 0.14% |
| 1246 | AATCACGG | 0.06% |
| 1250 | AATCGGGG | 6.36% |
| 1251 | AATCGGGT | 0.17% |
| 1252 | AATCGCAG | 1.03% |
| 1254 | AATCGCGG | 19.55% |
| Horned Haplotypes | | |
| 1030 | GCGCGCGG | 0.33% |
| 1058 | GCTCGGGG | 0.78% |
| 1090 | GAGCGGGG | 0.14% |
| 1094 | GAGCGCGG | 1.81% |
| 1108 | GATGGCAG | 0.31% |
| 1114 | GATCAGGG | 0.31% |
| 1118 | GATCACGG | 0.86% |
| 1119 | GATCACGT | 0.06% |
| 1122 | GATCGGGG | 4.41% |
| 1123 | GATCGGGT | 0.25% |

TABLE 4-continued

Eight-SNP Haplotypes and Percentage Representation in 4,171 Cattle of Various Breeds

| Designation | Actual Haplotype[1] | % |
|---|---|---|
| 1124 | GATCGCAG | 2.43% |
| 1126 | GATCGCGG | 13.14% |
| 1127 | GATCGCGT | 1.12% |
| Unknown Haplotype | | |
| 1125 | GATCGCAT | 1.34% |

[1]Marker Order: MMBT25287, MMBT25303, MMBT25281, MMBT25316, MMBT25314, MMBT25313, MMBT10493, MMBT25986

One haplotype (1125) listed above in Table 4 could not be assigned unambiguously.

Ambiguity was observed in only one haplotype that can be managed by breed. Haplotype 1122 is horned in the English and European breeds segregating at the locus, but a unique mutation associates it with polled in Jersey and Holstein cattle. Although the haplotypes have been observed to be highly predictive of horned/polled genotype in the population of cattle studied, it is expected in any genetic analysis that a small percentage of the results may be in error due to the appearance of new polymorphisms caused by random mutation and recombination.

Breeding analysis of the animals listed above confirmed that the 34 unambiguous eight-SNP haplotypes identified above bred true. Matings involving the animals listed in Table 4 produced offspring having the expected genotypes and phenotypes.

EXAMPLE 3

Development of a Six-SNP Haplotype System for Inferring Horned and Polled Phenotypes In subsequent analyses of the nucleotide occurrence of the SNPs described above (performed as described above in Example 1), more than 9,000 individual haplotypes from compiled from 6,360 Angus, Charolais, Gelbvieh, Hereford, Limousin and Simmental cattle have been determined. Based on this analysis, a six-SNP haplotype system was found sufficient to unambiguously infer the genotype of the vast majority of animals tested. The most prevalent haplotypes are listed in Table 5 by breed, number of haplotypes observed, and determination as to horned or polled phenotype. The markers of the six-SNP haplotypes: MMBT25287 (SEQ ID NO:53), MMBT25303(SEQ ID NO:59), MMBT25281(SEQ ID NO:52), MMBT25316 (SEQ ID NO:63), MMBT25314(SEQ ID NO:62), and MMBT25313(SEQ ID NO:61).

TABLE 5

Six-Marker Haplotypes for Horned or Polled Phenotypes

| 6 Marker Haplotype Pattern | MMBT 25287 | MMBT 25303 | MMBT 25281 | MMBT 25316 | MMBT 25314 | MMBT 25313 | Pheno-type | An-gus | Cha-rolais | Gelb-vieh | Here-ford | Limou-sin | Sim-mental | Totals |
|---|---|---|---|---|---|---|---|---|---|---|---|---|---|---|
| GCGCGC | G | C | G | C | G | C | H | 0 | 0 | 1 | 3 | 4 | 7 | 17 |
| GAGCGG | G | A | G | C | G | G | H | 0 | 0 | 2 | 5 | 12 | 5 | 24 |
| GAGCGC | G | A | G | C | G | C | H | 0 | 0 | 12 | 1 | 121 | 62 | 209 |
| GATGGC | G | A | T | G | G | C | H | 0 | 0 | 1 | 0 | 26 | 1 | 28 |
| GATCAC | G | A | T | C | A | C | H | 0 | 1 | 4 | 1 | 69 | 1 | 91 |
| GATCGC | G | A | T | C | G | C | H | 0 | 6 | 131 | 8 | 1413 | 89 | 1647 |
| GCTCAC | G | C | T | G | A | G | P | 1 | 1 | 14 | 0 | 2 | 0 | 31 |
| GCTCGC | G | C | T | C | G | C | P | 3 | 1 | 83 | 0 | 2162 | 153 | 2405 |
| GATGGG | G | A | T | G | G | G | P | 0 | 4 | 1 | 32 | 13 | 29 | 79 |
| AATGGG | A | A | T | G | G | G | P | 10 | 12 | 147 | 0 | 688 | 414 | 1271 |
| AATGGC | A | A | T | G | G | C | P | 29 | 2 | 92 | 0 | 236 | 141 | 500 |
| AATCAC | A | A | T | C | A | C | P | 3 | 9 | 5 | 52 | 39 | 29 | 137 |
| AATCGG | A | A | T | C | G | G | P | 0 | 0 | 17 | 2 | 595 | 10 | 624 |
| AATCGC | A | A | T | C | G | C | P | 34 | 12 | 213 | 3 | 1930 | 234 | 2426 |
| | | | | | | | Totals | 80 | 48 | 723 | 107 | 7310 | 1175 | 9489 |

EXAMPLE 4

Haplotype 1122

One additional haplotype (1122) that was detected in the animals listed in Table 4, above, proved to be ambiguous. That is, family structure was found to be required to determine whether this haplotype is in phase with horned or polled alleles. The polled version of this haplotype was identified in Limousin, Holstein and Jersey cattle. See Table 6, below.

Holstein and Jersey breeds are horned dairy breeds. Recently, however, new "polled" animals have appeared within these breeds. In each of 10 polled Jersey (n=20 Jersey, both horned and polled) and 46 polled Holstein (n=73, both horned and polled) animals analyzed, the 1122 haplotype was detected. However, the presence of the 1122 haplotype alone is insufficient to predict a polled phenotype since certain horned animals were observed with the 1122 horned haplotype, including 2 Holsteins.

Taken together, in order to determine whether an animal has a polled genotype based on detection of a 1122/GATCGG haplotype, it is necessary to analyze the parentage of the 1122 haplotype in addition to detecting the haplotype in the subject animal. A prediction of a polled phenotype is possible when the parental 1122 haplotype is from a polled animal, particularly a polled Limousin, Jersey or Holstein animal.

TABLE 6

Phenotype of Animals Having a 1122 (GATCGG) Haplotype

| | Number of Animals Observed Per Phenotype | |
|---|---|---|
| Breed | Horned | Polled |
| Angus | 0 | 0 |
| Charolais | 1 | 0 |
| Gelbvieh | 7 | 0 |
| Hereford | 82 | 0 |
| Holstein | 2 | 46 |
| Limousin | 79 | 37 |
| Simmental | 22 | 0 |
| Jersey | 0 | 10 |

The foregoing written specification is considered to be sufficient to enable one skilled in the art to practice the invention. The present invention is not limited in scope by the examples provided, since the examples are intended as illustrations of various aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. All references, patents and patent publications that are recited in this application are incorporated in their entirety herein by reference.

What is claimed is:

1. A method for determining a polled genotype in a bovine subject comprising:
   a) detecting in a nucleic acid sample isolated from the bovine subject, an AAT haplotype indicative of the polled phenotype, wherein the AAT haplotype comprises an A at position 300 of SEQ ID NO: 53 (marker MMBT25287), an A at position 300 of SEQ ID NO: 59 (marker MMBT25303), and a T at position 300 of SEQ ID NO: 52 (marker MMBT25281),
   wherein detection of the AAT haplotype is indicative of a polled genotype in the bovine subject.

2. The method of claim 1 wherein step a) further comprises measurement of a nucleotide occurrence of SNPs at position 300 of SEQ ID NO: 63 (marker MMBT25316), SEQ ID NO: 62 (marker MMBT25314), and SEQ ID NO: 61 (marker MMBT25313).

3. The method of claim 1 wherein step a) further comprises measurement of a nucleotide occurrence of SNPs at position 300 of SEQ ID NO: 63 (marker MMBT25316), SEQ ID NO: 62 (marker MMBT25314), SEQ ID NO: 61 (marker MMBT25313), SEQ ID NO: 50 (marker MMBT10493), and SEQ ID NO: 64 (marker MMBT25986).

4. The method of claim 1, comprising detecting a diploid pair of haplotype alleles.

5. The method of claim 1, wherein the bovine subject is a member of a breed selected from Angus, Charolais, Gelbvieh, Hereford, Limousin, or Simmental.

6. The method of claim 1, wherein the bovine subject is a member of a breed raised for beef production.

7. The method of claim 4, wherein the bovine subject is a member of a breed raised for beef and milk production.

8. The method of claim 2 wherein the haplotype is associated with a polled phenotype and is selected from: AATGGG, AATGGC, AATCAC, or AATCGC in a nucleic acid sample from the subject
wherein the sequence of letters of the haplotype represent the nucleotide occurrence of a single nucleotide polymorphism corresponding to nucleotide position 300 of SEQ ID NO: 53 (marker MMBT25287), SEQ ID NO: 59 (marker MMBT25303), SEQ ID NO: 52 (marker MMBT25281), SEQ ID NO: 63 (marker MMBT25316), SEQ ID NO: 62 (marker MMBT25314), and SEQ ID NO: 61 (marker MMBT25313) respectively.

9. The method of claim 3 further comprising detecting a polled haplotype selected from: AATCACGG, AATCACGG, AATGACGG, AATGGGAG, AATCGCGT, AATCGCGG, AATGGCGT, AATGGCGG, AATGGGGG AATGGGGT, AATCACAT, AATCGGGG, AATCGGGT or AATCGCAG in a nucleic acid sample from the subject
wherein the sequence of letters of the haplotype represent the nucleotide occurrence of a single nucleotide polymorphism corresponding to nucleotide position 300 of SEQ ID NO: 53 (marker MMBT25287), SEQ ID NO: 59 (marker MMBT25303), SEQ ID NO: 52 (marker MMBT25281), SEQ ID NO: 63 (marker MMBT25316), SEQ ID NO: 62 (marker MMBT25314), SEQ ID NO: 61 (marker MMBT25313), SEQ ID NO: 50 (marker MMBT10493), and SEQ ID NO: 64 (marker MMBT25986) respectively.

10. The method of claim 8, comprising detecting a diploid pair of haplotype alleles.

11. The method of claim 8, wherein the bovine subject is a member of a breed selected from Angus, Charolais, Gelbvieh, Hereford, Limousin, or Simmental.

12. The method of claim 8, wherein the bovine subject is a member of a breed raised for beef production.

13. The method of claim 11, wherein the bovine subject is a member of a breed raised for beef and milk production.

* * * * *

SEQUENCE LISTING

<160> NUMBER OF SEQ ID NOS: 66

<210> SEQ ID NO 1
<211> LENGTH: 26
<212> TYPE: DNA
<213> ORGANISM: Artificial Sequence
<220> FEATURE:
<223> OTHER INFORMATION: Forward Primer

<400> SEQUENCE: 1
acactaaacc aacagacaat aatgag                                              26

<210> SEQ ID NO 2
<211> LENGTH: 23
<212> TYPE: DNA
<213> ORGANISM: Artificial Sequence
<220> FEATURE:
<223> OTHER INFORMATION: Forward Primer

<400> SEQUENCE: 2
attatttagc ctaccacagt ccc                                                 23

<210> SEQ ID NO 3
<211> LENGTH: 24
<212> TYPE: DNA
<213> ORGANISM: Artificial Sequence
<220> FEATURE:
<223> OTHER INFORMATION: Forward Primer

<400> SEQUENCE: 3
atttttgttc ctattgtttt catg                                                24

<210> SEQ ID NO 4
<211> LENGTH: 22
<212> TYPE: DNA
<213> ORGANISM: Artificial Sequence
<220> FEATURE:
<223> OTHER INFORMATION: Forward Primer

<400> SEQUENCE: 4
atgttgcagt gaacaaaaca ga                                                  22

<210> SEQ ID NO 5
<211> LENGTH: 24
<212> TYPE: DNA
<213> ORGANISM: Artificial Sequence
<220> FEATURE:
<223> OTHER INFORMATION: Forward Primer

<400> SEQUENCE: 5
tctgtaaaca cagcagayct ttct                                                24

<210> SEQ ID NO 6
<211> LENGTH: 19
<212> TYPE: DNA
<213> ORGANISM: Artificial Sequence
<220> FEATURE:
<223> OTHER INFORMATION: Forward Primer

<400> SEQUENCE: 6
ttttccracc attttcagg                                                      19

<210> SEQ ID NO 7
<211> LENGTH: 23
<212> TYPE: DNA

```
<213> ORGANISM: Artificial Sequence
<220> FEATURE:
<223> OTHER INFORMATION: Forward Primer

<400> SEQUENCE: 7
aacacgtgaa gttttcagt ttc                                             23

<210> SEQ ID NO 8
<211> LENGTH: 18
<212> TYPE: DNA
<213> ORGANISM: Artificial Sequence
<220> FEATURE:
<223> OTHER INFORMATION: Forward Primer

<400> SEQUENCE: 8
tgaactgact gcgctggc                                                  18

<210> SEQ ID NO 9
<211> LENGTH: 25
<212> TYPE: DNA
<213> ORGANISM: Artificial Sequence
<220> FEATURE:
<223> OTHER INFORMATION: Forward Primer

<400> SEQUENCE: 9
ttgacaaatg taactgtaag gtttc                                          25

<210> SEQ ID NO 10
<211> LENGTH: 20
<212> TYPE: DNA
<213> ORGANISM: Artificial Sequence
<220> FEATURE:
<223> OTHER INFORMATION: Forward Primer

<400> SEQUENCE: 10
acttgatcct tgtctttgcc                                                20

<210> SEQ ID NO 11
<211> LENGTH: 24
<212> TYPE: DNA
<213> ORGANISM: Artificial Sequence
<220> FEATURE:
<223> OTHER INFORMATION: Forward Primer

<400> SEQUENCE: 11
aaacttgtct gttgtactca agca                                           24

<210> SEQ ID NO 12
<211> LENGTH: 22
<212> TYPE: DNA
<213> ORGANISM: Artificial Sequence
<220> FEATURE:
<223> OTHER INFORMATION: Forward Primer

<400> SEQUENCE: 12
tgtttgcaaa aggaagaaaa tg                                             22

<210> SEQ ID NO 13
<211> LENGTH: 18
<212> TYPE: DNA
<213> ORGANISM: Artificial Sequence
<220> FEATURE:
<223> OTHER INFORMATION: Forward Primer

<400> SEQUENCE: 13
ccaacacagt ccaacgca                                                  18
```

```
<210> SEQ ID NO 14
<211> LENGTH: 24
<212> TYPE: DNA
<213> ORGANISM: Artificial Sequence
<220> FEATURE:
<223> OTHER INFORMATION: Forward Primer

<400> SEQUENCE: 14
ttttatttct ctctcccact catg                                          24

<210> SEQ ID NO 15
<211> LENGTH: 22
<212> TYPE: DNA
<213> ORGANISM: Artificial Sequence
<220> FEATURE:
<223> OTHER INFORMATION: Forward Primer

<400> SEQUENCE: 15
aaacaatttc ataagccatc ct                                            22

<210> SEQ ID NO 16
<211> LENGTH: 18
<212> TYPE: DNA
<213> ORGANISM: Artificial Sequence
<220> FEATURE:
<223> OTHER INFORMATION: Forward Primer

<400> SEQUENCE: 16
tccatcctcg gaagggca                                                 18

<210> SEQ ID NO 17
<211> LENGTH: 24
<212> TYPE: DNA
<213> ORGANISM: Artificial Sequence
<220> FEATURE:
<223> OTHER INFORMATION: Reverse Primer

<400> SEQUENCE: 17
ttacaagtgt tccctttatg gagt                                          24

<210> SEQ ID NO 18
<211> LENGTH: 19
<212> TYPE: DNA
<213> ORGANISM: Artificial Sequence
<220> FEATURE:
<223> OTHER INFORMATION: Reverse Primer

<400> SEQUENCE: 18
tccaaggcat gtcaacatt                                                19

<210> SEQ ID NO 19
<211> LENGTH: 21
<212> TYPE: DNA
<213> ORGANISM: Artificial Sequence
<220> FEATURE:
<223> OTHER INFORMATION: Reverse Primer

<400> SEQUENCE: 19
aaaaggagac tccaggaaac a                                             21

<210> SEQ ID NO 20
<211> LENGTH: 21
<212> TYPE: DNA
<213> ORGANISM: Artificial Sequence
<220> FEATURE:
<223> OTHER INFORMATION: Reverse Primer
```

```
<400> SEQUENCE: 20
tttcartgga aagggaatc a                                              21

<210> SEQ ID NO 21
<211> LENGTH: 23
<212> TYPE: DNA
<213> ORGANISM: Artificial Sequence
<220> FEATURE:
<223> OTHER INFORMATION: Reverse Primer

<400> SEQUENCE: 21
agccaaagaa actgaaaaac ttc                                           23

<210> SEQ ID NO 22
<211> LENGTH: 18
<212> TYPE: DNA
<213> ORGANISM: Artificial Sequence
<220> FEATURE:
<223> OTHER INFORMATION: Reverse Primer

<400> SEQUENCE: 22
ttcaccccag gccagagg                                                 18

<210> SEQ ID NO 23
<211> LENGTH: 18
<212> TYPE: DNA
<213> ORGANISM: Artificial Sequence
<220> FEATURE:
<223> OTHER INFORMATION: Reverse Primer

<400> SEQUENCE: 23
agaagctgaa tggggcca                                                 18

<210> SEQ ID NO 24
<211> LENGTH: 19
<212> TYPE: DNA
<213> ORGANISM: Artificial Sequence
<220> FEATURE:
<223> OTHER INFORMATION: Reverse Primer

<400> SEQUENCE: 24
taacacatct tcccccctg                                                19

<210> SEQ ID NO 25
<211> LENGTH: 21
<212> TYPE: DNA
<213> ORGANISM: Artificial Sequence
<220> FEATURE:
<223> OTHER INFORMATION: Reverse Primer

<400> SEQUENCE: 25
acagacccat ttcacagact g                                             21

<210> SEQ ID NO 26
<211> LENGTH: 27
<212> TYPE: DNA
<213> ORGANISM: Artificial Sequence
<220> FEATURE:
<223> OTHER INFORMATION: Reverse Primer

<400> SEQUENCE: 26
tgagtaccat attgatccta aaaactg                                       27

<210> SEQ ID NO 27
<211> LENGTH: 23
<212> TYPE: DNA
```

```
<213> ORGANISM: Artificial Sequence
<220> FEATURE:
<223> OTHER INFORMATION: Reverse Primer

<400> SEQUENCE: 27
gcttagtagc tctgaggcat ctt                                          23

<210> SEQ ID NO 28
<211> LENGTH: 26
<212> TYPE: DNA
<213> ORGANISM: Artificial Sequence
<220> FEATURE:
<223> OTHER INFORMATION: Reverse Primer

<400> SEQUENCE: 28
tctctctttt ttaatgtttc acttgc                                       26

<210> SEQ ID NO 29
<211> LENGTH: 23
<212> TYPE: DNA
<213> ORGANISM: Artificial Sequence
<220> FEATURE:
<223> OTHER INFORMATION: Reverse Primer

<400> SEQUENCE: 29
ttgatcatcc tacacataac cgt                                          23

<210> SEQ ID NO 30
<211> LENGTH: 19
<212> TYPE: DNA
<213> ORGANISM: Artificial Sequence
<220> FEATURE:
<223> OTHER INFORMATION: Reverse Primer

<400> SEQUENCE: 30
atttcatgat gggcctcag                                               19

<210> SEQ ID NO 31
<211> LENGTH: 18
<212> TYPE: DNA
<213> ORGANISM: Artificial Sequence
<220> FEATURE:
<223> OTHER INFORMATION: Reverse Primer

<400> SEQUENCE: 31
ggggcaccaa ggtagtca                                                18

<210> SEQ ID NO 32
<211> LENGTH: 26
<212> TYPE: DNA
<213> ORGANISM: Artificial Sequence
<220> FEATURE:
<223> OTHER INFORMATION: Reverse Primer

<400> SEQUENCE: 32
tgactgacag ggactcattt tttatt                                       26

<210> SEQ ID NO 33
<211> LENGTH: 25
<212> TYPE: DNA
<213> ORGANISM: Artificial Sequence
<220> FEATURE:
<223> OTHER INFORMATION: Extension Primer

<400> SEQUENCE: 33
ggtccacttg atccttgtct ttgcc                                        25
```

```
<210> SEQ ID NO 34
<211> LENGTH: 25
<212> TYPE: DNA
<213> ORGANISM: Artificial Sequence
<220> FEATURE:
<223> OTHER INFORMATION: Extension Primer

<400> SEQUENCE: 34
acctctaggt aagctttcgt aaagc                                              25

<210> SEQ ID NO 35
<211> LENGTH: 25
<212> TYPE: DNA
<213> ORGANISM: Artificial Sequence
<220> FEATURE:
<223> OTHER INFORMATION: Extension Primer

<400> SEQUENCE: 35
ggcttctgtc tgtaaacaca gcaga                                              25

<210> SEQ ID NO 36
<211> LENGTH: 25
<212> TYPE: DNA
<213> ORGANISM: Artificial Sequence
<220> FEATURE:
<223> OTHER INFORMATION: Extension Primer

<400> SEQUENCE: 36
ctgcacatct tcatggagtt cacac                                              25

<210> SEQ ID NO 37
<211> LENGTH: 25
<212> TYPE: DNA
<213> ORGANISM: Artificial Sequence
<220> FEATURE:
<223> OTHER INFORMATION: Extension Primer

<400> SEQUENCE: 37
tttgtttcct ggagtctcct tttcc                                              25

<210> SEQ ID NO 38
<211> LENGTH: 25
<212> TYPE: DNA
<213> ORGANISM: Artificial Sequence
<220> FEATURE:
<223> OTHER INFORMATION: Extension Primer

<400> SEQUENCE: 38
gctgcgttga ctcattacag cgaaa                                              25

<210> SEQ ID NO 39
<211> LENGTH: 25
<212> TYPE: DNA
<213> ORGANISM: Artificial Sequence
<220> FEATURE:
<223> OTHER INFORMATION: Extension Primer

<400> SEQUENCE: 39
cagttcaccc caggccagag gccac                                              25

<210> SEQ ID NO 40
<211> LENGTH: 25
<212> TYPE: DNA
<213> ORGANISM: Artificial Sequence
<220> FEATURE:
<223> OTHER INFORMATION: Extension Primer
```

```
<400> SEQUENCE: 40
agcttcaagc tgcctgtgct agagg                                           25

<210> SEQ ID NO 41
<211> LENGTH: 25
<212> TYPE: DNA
<213> ORGANISM: Artificial Sequence
<220> FEATURE:
<223> OTHER INFORMATION: Extension Primer

<400> SEQUENCE: 41
tttgccactg ccacatccca gctra                                           25

<210> SEQ ID NO 42
<211> LENGTH: 25
<212> TYPE: DNA
<213> ORGANISM: Artificial Sequence
<220> FEATURE:
<223> OTHER INFORMATION: Extension Primer

<400> SEQUENCE: 42
atacctgctc cgtggcttgg ctctc                                           25

<210> SEQ ID NO 43
<211> LENGTH: 25
<212> TYPE: DNA
<213> ORGANISM: Artificial Sequence
<220> FEATURE:
<223> OTHER INFORMATION: Extension Primer

<400> SEQUENCE: 43
ggctcagtgg taaagaattt gcctg                                           25

<210> SEQ ID NO 44
<211> LENGTH: 25
<212> TYPE: DNA
<213> ORGANISM: Artificial Sequence
<220> FEATURE:
<223> OTHER INFORMATION: Extension Primer

<400> SEQUENCE: 44
agtttgtttt agccttttcc cctcc                                           25

<210> SEQ ID NO 45
<211> LENGTH: 25
<212> TYPE: DNA
<213> ORGANISM: Artificial Sequence
<220> FEATURE:
<223> OTHER INFORMATION: Extension Primer

<400> SEQUENCE: 45 gtggggcgg gccggtgccg cctcc                                            25

<210> SEQ ID NO 46
<211> LENGTH: 25
<212> TYPE: DNA
<213> ORGANISM: Artificial Sequence
<220> FEATURE:
<223> OTHER INFORMATION: Extension Primer

<400> SEQUENCE: 46
ctttgatttg agggatcagc ctgca                                           25

<210> SEQ ID NO 47
<211> LENGTH: 25
<212> TYPE: DNA
```

```
<213> ORGANISM: Artificial Sequence
<220> FEATURE:
<223> OTHER INFORMATION: Extension Primer

<400> SEQUENCE: 47
cctcccgggt ttctgagaac ctggc                                          25

<210> SEQ ID NO 48
<211> LENGTH: 25
<212> TYPE: DNA
<213> ORGANISM: Artificial Sequence
<220> FEATURE:
<223> OTHER INFORMATION: Extension Primer

<400> SEQUENCE: 48
gggcggagtg gagaggctgt tcctg                                          25

<210> SEQ ID NO 49
<211> LENGTH: 600
<212> TYPE: DNA
<213> ORGANISM: Bovine

<400> SEQUENCE: 49
ttttcttttt ttttaatata tgaaactaat cataacaagt ggttgctgtg aaaacagcag     60
gctccctaag gctgcccttc caatgaccca taccctgacc tggacagacc accttctttc    120
caagagagga gaagttttgt tcctagatca gatgaaactc tggctttacc cctggtgacc    180
aggaggatta atcagacgcc agtaaaacag ccgacagaca cactaaacca acagacaata    240
atgagcacac acaccaggaa acgtccgtcc aagaggtcca cttgatcctt gtctttgccy    300
taagatgtaa tacctgctcc gtggcttggc tctcygtact ccataaaggg aacacttgta    360
agctgagaag ctgccagttt ttaggatcaa tatggtactc acaagagctg gttaggaaac    420
aatgccaggg acagaatttg cagtgggggc ttgtgaggga ttaggctgtt tcctcaagat    480
ttacgtccca gtgcacagcc ggtgctgaaa cctgcacggc ccaccctgtg gctccagatg    540
aggtgaatgg aggtctcttt gggttttggt ttttcaaag taaaatcttc ccagtgtgca    600

<210> SEQ ID NO 50
<211> LENGTH: 600
<212> TYPE: DNA
<213> ORGANISM: Bovine
<220> FEATURE:
<221> NAME/KEY: misc_feature
<222> LOCATION: (576)..(600)
<223> OTHER INFORMATION: n is a, c, g, or t

<400> SEQUENCE: 50
cgggcatgcg cacagctgag tcacttcact gtacagcaga aattgcttga aaagcaatta     60
tattcccccc caaaccaatt atattccccc aaatttatat tttatattga aaaaactcag    120
tggattggca aacttaattc tatccttctt aattcttaat tctattcttg agactcagga    180
atctgaattc cttcttgcca cctaacctaa catattcatg ggttccaggg attaagaggg    240
ggacattatt tagcctacca cagtcccggg catcacctct aggtaagctt tcgtaaagcr    300
gaaatgcctc tttccccttt ctccaaatgt tgacatgcct tggagggcag gcaggcagtg    360
ggttggagaa acaggtatat ttagcaaaac tgattcagct ctgccctcac tgagatccag    420
tggatgaaat gttatttga agtagtatct gtcttttccc aaacagcact tcaggacttt    480
tgtggtgacc tctctaaaca cttcattttc attcatgagg aaatggagag ccaggcggga    540
aggacttctc cagggtttcc cagcggttcc ccagcnnnnn nnnnnnnnnn nnnnnnnnn    600
```

<210> SEQ ID NO 51
<211> LENGTH: 600
<212> TYPE: DNA
<213> ORGANISM: Bovine

<400> SEQUENCE: 51

| | | | | | |
|---|---|---|---|---|---|
| gaaaaaaaac | cccacccatt | tcatttggac | tgtgtactaa | gaataattgc | caccaatatt | 60 |
| gattggccct | tggggaccca | gctgaattta | aaaattgcag | actgtgaaat | cccagctgat | 120 |
| atagcctcgt | ggagcttgct | gcttatttgt | gacatgttcc | tatgtttaaa | cttacccaca | 180 |
| aaaactgtga | aattaatatc | ctcacgttga | gtacaatatg | gtgacacacc | cagctgacat | 240 |
| gcgcagctat | ttttgttcct | attgttttca | tgctggcttc | tgtctgtaaa | cacagcagay | 300 |
| ctttctgatg | atgaagcata | agtccatttg | tttcctggag | tctccttttc | craccatttt | 360 |
| caggggttgg | gccaacacgt | gaagttttc | agtttctttg | gctgcacrtt | tcgctgtaat | 420 |
| gagtcaacgc | agcagggtct | cccrgtggcc | tctggcctgg | ggtgaactga | ctgcgctggc | 480 |
| cccattcagc | ttctccttgg | ctatgcctrc | ctctagcaca | ggcagcttga | agctagacat | 540 |
| tcctgttaaa | agcagggggg | aagatgtgtt | agtttgccta | aatccacgta | atgaaggatg | 600 |

<210> SEQ ID NO 52
<211> LENGTH: 600
<212> TYPE: DNA
<213> ORGANISM: Bovine

<400> SEQUENCE: 52

| | | | | | |
|---|---|---|---|---|---|
| gttaagtctt | taccttatgg | atgagaaaac | agagattcag | aaaatctgaa | tctcttgaca | 60 |
| gagacacttg | acagagtcac | agagctttca | ttcacttaaa | agtcaatgag | agaatgagaa | 120 |
| aaagtatttg | aatcaccact | tcactgaatt | attcaacata | tgtaactctt | tcttattgga | 180 |
| ttccctcatt | cattcattct | acaaatattt | actgagtgcc | tagtatgtgc | ccatcactgc | 240 |
| tgaggatgtt | gcagtgaaca | aaacagacaa | agaactgcac | atcttcatgg | agttcacack | 300 |
| ccaaggattc | aataaaattt | aaatccctga | ttcccttttc | caytgaaagg | tcgctatttt | 360 |
| aacaattcta | agaaaccact | tgattagcat | caaagatgtt | gaacaaatgc | tctgttgaca | 420 |
| taatttgatg | agtgtaggaa | ttacaaatat | gagtcaacty | cactgattac | aaagacagaa | 480 |
| gaaagtagtg | tacaatcaac | ttttttagaa | aagaattaaa | ccccatgaaa | aaacaatgtt | 540 |
| ccaacatgac | atccagattc | accagcyatg | tctcctgaaa | cagaggagaa | gactgttagg | 600 |

<210> SEQ ID NO 53
<211> LENGTH: 600
<212> TYPE: DNA
<213> ORGANISM: Bovine

<400> SEQUENCE: 53

| | | | | | |
|---|---|---|---|---|---|
| ccaatattga | ttggcccttg | gggacccagc | tgaatttaaa | aattgcagac | tgtgaaatcc | 60 |
| cagctgatat | agcctcgtgg | agcttgctgc | ttatttgtga | catgttccta | tgtttaaact | 120 |
| tacccacaaa | aactgtgaaa | ttaatatcct | cacgttgagt | acaatatggt | gacacaccca | 180 |
| gctgacatgc | gcagctattt | tgttcctat | tgttttcatg | ctggcttctg | tctgtaaaca | 240 |
| cagcagayct | ttctgatgat | gaagcataag | tccatttgtt | tcctggagtc | tccttttccr | 300 |
| accattttca | ggggttgggc | caacacgtga | agttttcag | tttctttggc | tgcacrtttc | 360 |
| gctgtaatga | gtcaacgcag | cagggtctcc | crgtggcctc | tggcctgggg | tgaactgact | 420 |
| gcgctggccc | cattcagctt | ctccttggct | atgcctrcct | ctagcacagg | cagcttgaag | 480 |

| | |
|---|---|
| ctagacattc ctgttaaaag cagggggggaa gatgtgttag tttgcctaaa tccacgtaat | 540 |
| gaaggatgac tacgtagact tgcacgtaca tggattgcaa gcttcaaata tgtcaaggat | 600 |

<210> SEQ ID NO 54
<211> LENGTH: 600
<212> TYPE: DNA
<213> ORGANISM: Bovine

<400> SEQUENCE: 54

| | |
|---|---|
| atcccagctg atatagcctc gtggagcttg ctgcttattt gtgacatgtt cctatgttta | 60 |
| aacttaccca caaaaactgt gaaattaata tcctcacgtt gagtacaata tggtgacaca | 120 |
| cccagctgac atgcgcagct atttttgttc ctattgtttt catgctggct tctgtctgta | 180 |
| aacacagcag ayctttctga tgatgaagca taagtccatt tgtttcctgg agtctccttt | 240 |
| tccraccatt ttcaggggtt gggccaacac gtgaagtttt tcagtttctt tggctgcacr | 300 |
| tttcgctgta atgagtcaac gcagcagggt ctcccrgtgg cctctggcct ggggtgaact | 360 |
| gactgcgctg gccccattca gcttctcctt ggctatgcct rcctctagca caggcagctt | 420 |
| gaagctagac attcctgtta aaagcagggg gaagatgtg ttagtttgcc taaatccacg | 480 |
| taatgaagga tgactacgta gacttgcacg tacatggatt gcaagcttca aatatgtcaa | 540 |
| ggatggaaat tcaaatgtt tctgaaatga gtcacaacta aaaatgaaaa gttaatccta | 600 |

<210> SEQ ID NO 55
<211> LENGTH: 600
<212> TYPE: DNA
<213> ORGANISM: Bovine

<400> SEQUENCE: 55

| | |
|---|---|
| atttgtgaca tgttcctatg tttaaactta cccacaaaaa ctgtgaaatt aatatcctca | 60 |
| cgttgagtac aatatggtga cacacccagc tgacatgcgc agctattttt gttcctattg | 120 |
| ttttcatgct ggcttctgtc tgtaaacaca gcagaycttt ctgatgatga agcataagtc | 180 |
| catttgtttc ctggagtctc cttttccrac cattttcagg ggttgggcca acacgtgaag | 240 |
| ttttttcagtt tctttggctg cacrtttcgc tgtaatgagt caacgcagca gggtctcccr | 300 |
| gtggcctctg gcctggggtg aactgactgc gctggcccca ttcagcttct ccttggctat | 360 |
| gcctrcctct agcacaggca gcttgaagct agacattcct gttaaaagca ggggggaaga | 420 |
| tgtgttagtt tgcctaaatc cacgtaatga aggatgacta cgtagacttg cacgtacatg | 480 |
| gattgcaagc ttcaaatatg tcaaggatgg aaatttcaaa tgtttctgaa atgagtcaca | 540 |
| actaaaaatg aaaagttaat cctacgtatc cttccttctt acgtcatgaa gatgtacact | 600 |

<210> SEQ ID NO 56
<211> LENGTH: 600
<212> TYPE: DNA
<213> ORGANISM: Bovine

<400> SEQUENCE: 56

| | |
|---|---|
| agtacaatat ggtgacacac ccagctgaca tgcgcagcta ttttttgttcc tattgttttc | 60 |
| atgctggctt ctgtctgtaa acacagcaga yctttctgat gatgaagcat aagtccattt | 120 |
| gtttcctgga gtctcctttt ccraccattt tcaggggttg gccaacacg tgaagttttt | 180 |
| cagtttcttt ggctgcacrt ttcgctgtaa tgagtcaacg cagcagggtc tcccrgtggc | 240 |
| ctctggcctg gggtgaactg actgcgctgg ccccattcag cttctccttg gctatgcctr | 300 |
| cctctagcac aggcagcttg aagctagaca ttcctgttaa aagcaggggg gaagatgtgt | 360 |

```
tagtttgcct aaatccacgt aatgaaggat gactacgtag acttgcacgt acatggattg      420
caagcttcaa atatgtcaag gatggaaatt tcaaatgttt ctgaaatgag tcacaactaa      480
aaatgaaaag ttaatcctac gtatccttcc ttcttacgtc atgaagatgt acactttcaa      540
ccaagcaaaa catataaaca actctgatgg tgaaattttc agggcgccac ggattgttac      600
```

<210> SEQ ID NO 57
<211> LENGTH: 606
<212> TYPE: DNA
<213> ORGANISM: Bovine
<220> FEATURE:
<221> NAME/KEY: misc_feature
<222> LOCATION: (1)..(6)
<223> OTHER INFORMATION: n is a, c, g, or t

<400> SEQUENCE: 57

```
nnnnnnctct ttaatttaca attttctacc tgttacctgg tacctggtac cagataagag       60
aaaatacatt ttttttaaact aaatttcttg tctacatata aaccttccca caaaacttcg     120
ctatgggtta aatatgtatc cagccttgtg atgagcactg ggggatgaag acttagcaac     180
caagaggtaa aggtcctaac cacaggaaac taagatgctc ttttaaattt taaccatata     240
aggcagagtt gacaaatgta actgtaaggt ttcctttgcc actgccacat cccagctrar     300
ttgcataact caacttctca atttcacagt ctgtgaaatg ggtctgtgag tcaaatctac     360
tcyagcatag gcatggggat gaaatgcctg gaaagatcca atctgggcac acagtcttca     420
cctcccctgt gtgatgggga acaagcacag trggaaattc atgggaagga agcttgcca     480 tgggctgagc tatgtagggg ggaccagagg aggggttgag gattgacttg agagcatgag     540
gtagcccggg ataacataga tcattttgat ccaaattgct gctgcgagcc tgtgataatt     600
gggtga                                                                606
```

<210> SEQ ID NO 58
<211> LENGTH: 600
<212> TYPE: DNA
<213> ORGANISM: Bovine

<400> SEQUENCE: 58

```
caagtggttg ctgtgaaaac agcaggctcc ctaaggctgc ccttccaatg acccataccc       60
tgacctggac agaccacctt ctttccaaga gaggagaagt tttgttccta gatcagatga     120
aactctggct ttacccctgg tgaccaggag gattaatcag acgccagtaa aacagccgac     180
agacacacta aaccaacaga caataatgag cacacacacc aggaaacgtc cgtccaagag     240
gtccacttga tccttgtctt tgccytaaga tgtaatacct gctccgtggc ttggctctcy     300
gtactccata aagggaacac ttgtaagctg agaagctgcc agttttagg atcaatatgg      360 tactcacaag agctggttag gaaacaatgc cagggacaga atttgcagtg ggggcttgtg     420
agggattagg ctgtttcctc aagatttacg tcccagtgca cagccggtgc tgaaacctgc     480
acggcccacc ctgtggctcc agatgaggtg aatggaggtc tctttgggtt ttggtttttt     540
caaagtaaaa tcttcccagt gtgcaaacag gaaccactaa cactgaacca catgcagatg     600
```

<210> SEQ ID NO 59
<211> LENGTH: 600
<212> TYPE: DNA
<213> ORGANISM: Bovine

<400> SEQUENCE: 59

```
aaggacttgc tcctgatttt cctgaggatc tctaccattt aattaagaaa gccgttgcgg       60
```

```
tttgaaagca tcttgagagg aaaagaaagg ataaagatgc tcaattgcat ctgattctga      120
ttgacagccc cattcactgg tgggctggat attacaagac caaacaagtc cttccctca       180 accggaaata cacatctgca gcatttggct tgattgcata aacttgtctg ttgtactcaa      240
gcaataaaac tagaaagaaa gggrtttccc aggtggctca gtggtaaaga atttgcctgm      300
caatgcagga gatacggatt cgatycctgg gccaggaaga tgcctcagag ctactaagcc      360
caagcactac aattactgag mccaygtgcc acaagcctga cacccctaga gtgtakgctc      420
caccacaaaa gaagctccca cagcgaggag ccttcacacc acaactggac tgtcacctcr      480
cctagcagca actagagaaa agtctgcaca gcaataaaga cccagcacag ccataaataa      540
aattattttt taaggactag gaaaaaaaa agaaagaaaa tatatccaaa atatgaccac       600

<210> SEQ ID NO 60
<211> LENGTH: 600
<212> TYPE: DNA
<213> ORGANISM: Bovine
<220> FEATURE:
<221> NAME/KEY: misc_feature
<222> LOCATION: (554)..(600)
<223> OTHER INFORMATION: n is a, c, g, or t

<400> SEQUENCE: 60
tgaaacagtc tgttcattat acagtcgtag gacggaagat ttagcgctcc catacccgg       60 gacccgggca ggttaccgtt tttagacgga cagttgacaa agaatgaat agctctctcc      120 tgtcaaatca ggcttacaaa cagcttggca tacaaacagt tactacttgt atgcatgcgg     180
atttagggtc cccacctgct aatgcccag atttgtaagt acaaattggt tagtcttcaa     240
actgtttgca aaaggaagaa aatgaccaaa aattagtttg ttttagcctt ttcccctccm     300
ctcccctccc tgctcctgca agtgaaacat taaaaaagag agagagacag acagaagaaa    360
aggataaaat agtatgtaat agtctcgtgg aatattgttg gctttttta cttaaggcat    420 cgaatgaagc tggatcattg tttggtagga aatatttttg tgctgctcag gcatcctgct    480
tctcagcaag cagctgaaaa tctaatagaa ttaattgaag acctgtgatg ttaaaagatg    540
gaggggagga gatnnnnnnn nnnnnnnnn nnnnnnnnnn nnnnnnnnn nnnnnnnnn        600

<210> SEQ ID NO 61
<211> LENGTH: 600
<212> TYPE: DNA
<213> ORGANISM: Bovine

<400> SEQUENCE: 61
catttacacg gaaagctttt tcttttactt tgggatgcag agtaactccc aaattacaga      60
gccacttggc gattaaggca ggatggaggt gcatttgata acttaatgca actttttacc     120
agcacttaaa actcagatat gaaatctaca cttgatcttt cctgcttgga attggccaaa    180
ttagtggctg tatccccatg tacaacaaaa gcctctcaga acactcagg gaagccgacc     240 aaccaagggg cccaacacag tccaacgcaw gcatgtgggg gcggccggt gccgcctccs    300 cctcgagccc ctcaaacagc ctttcggctc cagacggtta tgtgtaggat gatcaagggt    360
agacgtgata cgctcaaggt agaaatgagg acttcagggc atgccttgcg agctttctcc    420
agttaattgg aaaattatat agtgatttca ctgctcataa caataaaacc ttctctttta    480
actttaaaga tgatgatgac tggtgagcag cactataaac ctcagaaagt tgtctagaag    540
gttaaaatga ctggactgga tttagggaa gggcagattt gctgcacttt ttaaaaaaac    600

<210> SEQ ID NO 62
```

```
<211> LENGTH: 600
<212> TYPE: DNA
<213> ORGANISM: Bovine

<400> SEQUENCE: 62
tctttgcatg tgtggttctc tcccgccccc atctaaatat ttttattaaa aaaaatcatg      60
aaaaaatgtt agccccactc tatcacctca atcctagttt ttttctattt tgaaatggca     120
accaggggca ccctttcag ccagacaagc actggtgtcc ctagcaaaca agagctaaat      180
tccaggatgg ggaggaagaa caaggaaagc tagtccacac ctcccatcgc ccccatgccc     240
cccttttatt tctctctccc actcatgttt ttattccact tttctctcct ggattggacr     300
tgcaggctga tccctcaaat caaagttttc cagttgtcat ctgaggccca tcatgaaatc     360
agtttagtga gtcacgatta gaattaaaa aaaaaaaaa aaagaatag ttcagaaaac        420 atcaaagcac atcatacaaa gtaaagataa acactgttta ataacggatt ccttttagtt     480
gtgtgtggtt atgttgggcc aaaaggcaaa atgttttct tactctgggt tgcgatcaaa     540
ccattctgaa attccctgaa ggagaaggcg agagcagtaa acatcagggc aaaggtggcc     600

<210> SEQ ID NO 63
<211> LENGTH: 600
<212> TYPE: DNA
<213> ORGANISM: Bovine

<400> SEQUENCE: 63
aggaccactg cccttggtat cagtggagct tttgtggaaa gtgaccccct ggtgcccctg      60
tctgggcata ttggtggggg gtggcgtcct gtggtcggga ccactgccct cgggtgaccc     120 cggggggctgg tggaccctca caccgcctgt gggcctgggc cctcctggg gaggcccgat     180 acatgtgatg ggggtttctg acttggaaac aatttcataa gccatcctgg gagtaggtaa     240
ggcaagaggg gccccagaa cctcaggggcc cgatcctccc gggtttctga aacctggcs     300 gctgttttct ttccccccaac agacatgact acctttggtgc ccccagtggc ccccaagctg     360
caaatccaga agcctctccc atctgactcc tgagtcatgc ctgactttgc accacgtcca     420
cgggtctcct ctgtcctggc tccctcgcag cttctggttg ctgttttctc ttcatcttgc     480
tgcttaaatc cagtgtttca ccaagtgtgt tagcatcagc tctcttctct ttctgttctt     540
tcttccttgt catttatct tctctgccaa ataccagctt ccactctcta cagataattc      600

<210> SEQ ID NO 64
<211> LENGTH: 600
<212> TYPE: DNA
<213> ORGANISM: Bovine

<400> SEQUENCE: 64
aacacttcta caaaattagg tcagtcatat acttttataa tcagcttttg tacttaataa      60
attagacttt tartctgttc catatattct tctgcatgtt ttaacaattg tgtcacacag     120
caggtggggr cagcttgtcc tcacaggctc tgtcagcacc ctctcagccc gctaccatga     180
gcctcctcac aggagcacgt tcatacgcac agcctgcctg gggctcagct gtgctggggt     240
gaagctttgg gtactccatc ctcggaaggg cacagggcgg agtggagagg ctgttcctgk     300
aaacctgaga acactggcaa taaaaaatga gtccctgtca gtcaaataag tatcctgtct     360
ggtggtgctg tatatgtttt catgtgtttg tggtcatttt actttctcat tgatgtgtt      420 ttacttggca gttcttatgg tgtgcaaggg ttttgggtt tttttttta gttgatttgt      480 aggagccagt ttatgttaag gatcagaacc tctgtataat cctactttt cctactgggc       540
```

```
catttgtatc ttgattctct gtttttgttt ttaattgaag gataattgct ttacaatatt      600

<210> SEQ ID NO 65
<211> LENGTH: 24
<212> TYPE: DNA
<213> ORGANISM: Artificial Sequence
<220> FEATURE:
<223> OTHER INFORMATION: Forward Primer

<400> SEQUENCE: 65
tttttgttcc tattgttttc atgc                                             24

<210> SEQ ID NO 66
<211> LENGTH: 21
<212> TYPE: DNA
<213> ORGANISM: Artificial Sequence
<220> FEATURE:
<223> OTHER INFORMATION: Reverse Primer

<400> SEQUENCE: 66
agactccagg aaacaaatgg a                                                21
```